(12) United States Patent
Chanteloup et al.

(10) Patent No.: US 6,265,587 B1
(45) Date of Patent: Jul. 24, 2001

(54) INTERMEDIARY COMPOUNDS FOR THE HEMISYNTHESIS OF TAXANES AND PREPARATION PROCESSES THEREFOR

(75) Inventors: Luc Chanteloup, Sargé-lès-Le Mans; Bruno Chauveau, Le Mans; Christine Corbin, Etival-lès-Le Mans; Robert Dhal, Le Mans; Sonia Le Guen, Reims; Arnaud Lamy, La Milesse; Antoine Leze; Jean-Pierre Robin, both of Le Mans, all of (FR)

(73) Assignee: Societe d'Etude et de Recherche en Ingenierie Pharmaceutique Seripharm, Le Mans (FR)

( * ) Notice: Subject to any disclaimer, the term of this patent is extended or adjusted under 35 U.S.C. 154(b) by 0 days.

(21) Appl. No.: 09/065,041
(22) PCT Filed: Oct. 25, 1996
(86) PCT No.: PCT/FR96/01676
§ 371 Date: Apr. 27, 1998
§ 102(e) Date: Apr. 27, 1998
(87) PCT Pub. No.: WO97/15562
PCT Pub. Date: May 1, 1997
(Under 37 CFR 1.47)

(30) Foreign Application Priority Data

Oct. 27, 1995 (FR) .................................................. 95/12739

(51) Int. Cl.$^7$ ..................................................... C07D 263/14
(52) U.S. Cl. .......................... 548/237; 548/229; 548/230; 548/239
(58) Field of Search .................................... 548/237, 239, 548/229, 230

(56) References Cited

U.S. PATENT DOCUMENTS

| 4,876,399 | 10/1989 | Holton et al. | 568/817 |
| 5,463,106 | 10/1995 | Correa et al. | 560/39 |
| 5,578,739 | 11/1996 | Hittinger | 549/510 |

FOREIGN PATENT DOCUMENTS

| WO91/13066 | 9/1991 | (WO) . |
| WO93/10076 | 5/1993 | (WO) . |

*Primary Examiner*—Ba K. Trinh
(74) *Attorney, Agent, or Firm*—Finnegan, Henderson, Farabow, Garrett, & Dunner L.L.P.

(57) ABSTRACT

The present invention relates to new intermediates for the semisynthesis of taxanes and their preparation processes. It relates to derivatives of oxazolidines or oxazolidinones, as well as to new derivatives of baccatine III. The general process for the synthesis of taxanes according to the invention enables to obtain a product such as PACLITAXEL in only five steps from products available in the market, compared to nine steps in general, for processes of the prior art.

23 Claims, No Drawings

INTERMEDIARY COMPOUNDS FOR THE HEMISYNTHESIS OF TAXANES AND PREPARATION PROCESSES THEREFOR

This application is a 371 of PCT/FR96/01679, dated Oct. 25, 1996.

The present invention relates to novel intermediates for the hemisynthesis of taxanes and to their processes of preparation.

Taxanes, natural substances with a diterpene skeleton which is generally esterified by a β-amino acid side chain derived from N-alkyl- or N-aroylphenylisoserine, are known as anticancer agents. Several dozen taxanes have been isolated from Taxaceae of the genus Taxus, such as, for example, paclitaxel ($R_1$=Ac, $R_2$=Ph, $R_3$=$R_4$=H), cephalomanine, their derivatives deacetylated in the 10 position, or baccatins (derivatives without side chain) represented by the formulae 1 and 2 below.

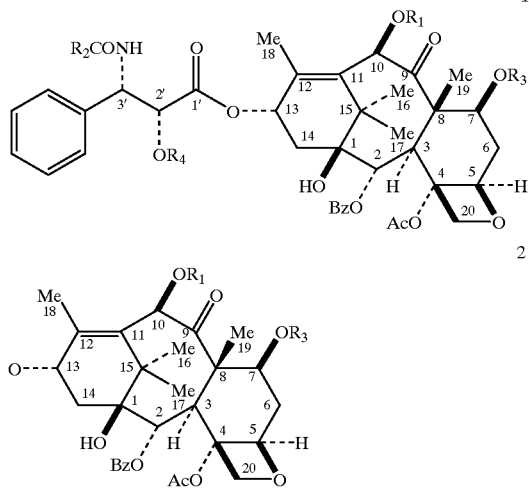

To avoid rapidly exhausting its original source, *Taxus brevifolia*, French researchers have sought to isolate paclitaxel from renewable parts (leaves) of *T. baccata*, the European yew. They have thus demonstrated the probable biogenetic precursor of taxanes, 10-deacetylbaccatin III, the springboard of choice for the hemisynthesis because of its relative abundance in leaf extracts.

The hemisynthesis of taxanes, such as paclitaxel or docetaxel ($R_1$=Ac, $R_2$=t-butyloxy, $R_3$=$R_4$=H), thus consists in esterifying the 13-hydroxyl of a protected derivative of baccatin or of 10-deacetylbaccatin III with a β-amino acid derivative.

Various processes for the hemisynthesis of paclitaxel or of docetaxel are described in the state of the art (EP-0 253 738, EP-0 336 840, EP-0 336 841, EP-0 495 718, WO 92/09589, WO 94/07877, WO 94/07878, WO 94/07879, WO 94/10169, WO 94/12482, EP-0 400 971, EP-0 428 376, WO 94/14787). Two recent works, I. Georg, T. T. Chen, I. Ojima, and D. M. Vyas, "Taxane Anticancer Agents, Basic Science and Current Status", ACS Symposium Series 583, Washington (1995) and Matthew Suffness, "Taxol® Science and Applications" CRC Press (1995), 1500 references cited, comprise exhaustive compilations of hemisyntheses of taxanes.

The β-amino acid side chains derived from N-alkyl- or N-aroylphenylisoserine of paclitaxel or docetaxel are of (2R,3S) configuration and one of the main difficulties in the hemisynthesis of taxanes is to obtain an enantiomerically pure product. The first problem consists in obtaining a pure enantiomer of the phenylisoserine derivatives employed in the hemisynthesis of taxanes. The second problem consists in retaining this enantiomeric purity during the esterification of the baccatin derivative and the subsequent treatments of the products obtained including deprotection of the hydroxyls and similar treatments.

Many studies on asymmetric synthesis involving derivatives of β-amino acids have focused on the chemistry of isoserine and of its derivatives, β-amino acids for which a dehydrated cyclic form is a β-lactam (EP-0 525 589). The majority of the various syntheses of phenylisoserine derivatives useful as precursors of taxane side chains focus on a common intermediate, (2R,3R)-cis-β-phenylglycidic acid, which is subsequently converted to β-phenylisoserine by reaction with ammonia (EP-0 495 718) or a nucleophile (Gou et al., *J. Org. Chem.*, 1983, 58, 1287–89). These various processes require a large number of stages in order to produce β-phenylisoserine of (2R,3S) configuration, necessarily with a stage of racemic resolution by conventional selective crystallization techniques, either for cis-β-phenylglycidic acid or for β-phenylisoserine, or subsequently, after conversion. Furthermore, in order to retain the enantiomeric purity of taxane side chain precursors during the esterification of the baccatin derivative, various means have been provided, in particular by using cyclic intermediates of blocked configuration, which remove the risks of isomerization during esterification reactions under severe reaction conditions. In particular, they involve 13lactam (EP-0 400 971), oxazolidine (WO 92/09589, WO 94/07877, WO 94/07878, WO 94/07879, WO 94/10169, WO 94/12482), oxazinone (EP-0 428 376) or oxazoline (WO 94/14787) derivatives. These cyclic precursors are prepared from the corresponding β-phenylisoserine derivative. As for the latter, the processes provided involve a large number of stages and a necessary racemic resolution in order to obtain the desired taxane side chain precursor. It was thus important to develop a novel route for the improved synthesis of intermediates which are taxane side chain precursors, in particular of enantiomers of cis-β-phenylglycidic acid, of β-phenylisoserine and of their cyclic derivatives.

Finally, for the hemisynthesis of taxanes and in particular of paclitaxel, the sole appropriate baccatin derivative used until now is that for which the 7-hydroxy radical is protected by a trialkylsilyl (EP-0 336 840, WO 94/14787), the deprotection of which is carried out exclusively in acidic medium. It was thus also important to employ novel protective groups for the hydroxyl functional group which in particular make possible selective protection of the 7-hydroxy radical and in addition allow a wider choice of operating conditions for the deprotection stage.

The present invention relates first of all to an improved process for the preparation of taxane side chain precursors.

The process according to the invention comprises converting a cis-β-arylglycidate derivative of general formula I

I

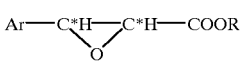

in which
Ar represents an aryl, in particular phenyl, and
R represents a hydrocarbon radical, preferably a linear or branched alkyl or a cycloalkyl optionally substituted by one or more alkyl groups, wherein said process is carried out so as to regio- and stereospecifically introduce the β-N-alkylamide and the a-hydroxyl or their cyclic precursors in a single stage by a Ritter reaction. Depending on the reaction mixture, two types of Ritter reaction are thus distinguished: one with opening of the oxetane, resulting in a linear form of the chain which is directly and completely functionalized, the other resulting in the direct formation of an oxazoline. The "*" symbol indicates the presence of an asymmetric carbon, with an R or S configuration. In both cases, the Ritter reaction is stereospecific, with retention of C-2 configuration and inversion of C-3 configuration. The process according to the invention is advantageously carried out on one of the enantiomers of the cis-β-arylglycidate derivative of general formula 1, so as to obtain the corresponding enantiomer of the linear chain or of the oxazoline, without subsequently requiring a racemic resolution. According to the method of preparation of the cis-β-arylglycidate derivative of general formula I described below, R represents an optically pure enantiomer of a highly sterically hindered chiral hydrocarbon radical, advantageously a cycloalkyl substituted by one or more alkyl groups, in particular a cyclohexyl. R will then preferably be one of the enantiomers of the menthyl radical, in particular (+) menthyl.

1. Direct synthesis of the linear chain

The direct synthesis of the linear chain by the Ritter reaction comprises reacting a cis-β-arylglycidate derivative of general formula I defined above with a nitrile of formula

in which

R$_2$ represents an aryl radical, preferably a phenyl, in the presence of a proton acid, such as sulphuric acid, perchloric acid, tetrafluoroboric acid, and the like, and of water.

A β-arylisoserine derivative of general formula IIa

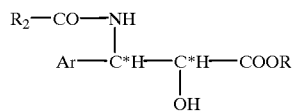

in which Ar, R and R$_2$ are defined above, is then obtained.

The reaction is carried out with inversion of the configuration of the C-3 of the cis-β-phenylglycidate derivative. Thus, starting from a (2R,3R)-cis-β-phenylglycidate derivative, the corresponding β-arylisoserine derivative of (2R,3S) configuration is obtained.

The Ritter reaction is carried out in an appropriate solvent, at a temperature ranging from −75 to +25° C.

The appropriate solvent can be the nitrile itself, when it is liquid at the reaction temperature, or alternatively the acid itself (sulphuric, perchloric or tetrafluoroboric), or a solvent, such as, for example, methylene chloride or ethyl ether. The proton acids conventionally used can contain the water necessary for the hydrolysis.

When benzonitrile (R$_2$=phenyl) is employed with the cis-β-arylglycidate of general formula I of (2R,3R) configuration for which Ar represents a phenyl, then the corresponding β-arylisoserine derivative of general formula IIa of (2R,3S) configuration for which Ar and R$_2$ represent a phenyl is directly obtained, which product is none other than the precursor of the side chain of paclitaxel.

2. Direct synthesis of the cyclic chain

In this method, a Ritter reaction is also carried out with a nitrile of formula

in which R′$_2$ represents R$_2$ defined above or a lower alkyl or lower perhaloalkyl radical, such as trichloromethyl, in the presence of a Lewis acid, in particular the boron trifluoride acetic acid complex, boron trifluoride etherate, antimony pentachloride, tin tetrachloride, titanium tetrachloride, and the like, or of a proton acid, such as, for example, tetrafluoroboric acid, the reaction being carried out in anhydrous medium.

As for the synthesis of the linear chain, the solvent can be the nitrile itself, when it is liquid at the reaction temperature, or alternatively an appropriate solvent, such as, for example, methylene chloride or ethyl ether. The reaction temperature also ranges from −75 to +25° C.

In the absence of water, an intramolecular Ritter reaction is carried out and the oxazoline of general formula IIb

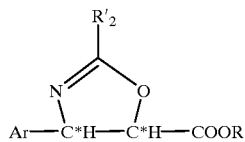

in which Ar, R and R′$_2$ are as defined above, is obtained.

As in the Ritter reaction in the presence of water, the reaction is carried out with inversion of the configuration of the C-3 of the cis-β-phenylglycidate derivative. Thus, starting from a (2R,3R)-cis-β-phenylglycidate derivative, the corresponding oxazoline of (2R, 3S) configuration is obtained.

For both Ritter reactions, in order to avoid the formation of a free carbocation which is the cause of many potential side reactions, the reactants are preferably added in the following order: i) the complex between the nitrile and the acid is first formed, then ii) the acid catalyst is added to the mixture composed of the oxirane and the nitrile.

The products obtained by this first stage, which are β-arylisoserine derivatives of general formula Ia or oxazoline derivatives of general formula IIb, can be further converted in a second optional stage described hereinbelow or then converted to acids by controlled saponification, before being coupled to a protected baccatin derivative for the hemisynthesis of taxanes, in particular of paclitaxel and its 10-deacetylated derivatives or of docetaxel. In the case of β-arylisoserine derivatives of general formula IIa, the saponification can be preceded by a conventional stage of protection of the hydroxyl by an appropriate protective group. A derivative of general formula II′a

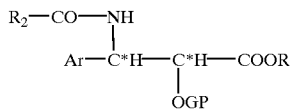

in which

Ar, R and R$_2$ are defined above, and

GP represents a protective group for the hydroxyl functional group which is appropriate for the synthesis of taxanes, in particular chosen from alkoxy ether, aralkoxy ether, aryloxy ether or haloalkoxycarbonyl radicals, such as, for example, methoxymethyl, 1-ethoxyethyl, benzyloxymethyl or (β-trimethylsilylethoxy)methyl groups, tetrahydropyranyl or β-alkoxycarbonyl (TrOC) radicals, β-halogenated or alkylsilyl ethers or alkoxyacetyl, aryloxyacetyl, haloacetyl or formyl radicals, is then obtained.

3. Conversion of the derivatives of formula IIa or IIb

The derivatives of general formula IIa or IIb obtained above can optionally be converted into novel intermediates which are side chain precursors in the hemisynthesis of taxanes. These conversions take place with retention of the configuration of the C-2 and C-3 positions. The novel intermediates obtained will thus have the same stereochemistry as the derivatives of formula IIa or IIb from which they derive. The products obtained in this second stage are subsequently converted into acids by controlled saponification, before being coupled with a protected baccatin derivative for the hemisynthesis of taxane, in particular of paclitaxel or of docetaxel.

3.1 Cyclization of the derivatives of general formula IIa

The derivatives of general formula IIa can subsequently be converted into oxazolines of formula IIb according to conventional methods of the state of the art (WO 94/14787).

The β-arylisoserine derivatives of general formula Ia can also be converted into novel oxazolidinone cyclic intermediates of general formula III'a

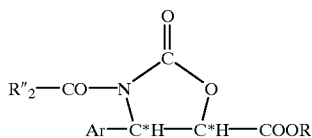

III'a in which Ar and R are defined above and R"$_2$ represents R'$_2$ defined above, an alkoxy radical, preferably a t-butoxy radical, or a linear or branched alkyl radical comprising at least one unsaturation, for example a 1-methyl-1-propylene radical, and the corresponding dialkyl acetals.

The oxazolidinones of general formula III'a are obtained first of all by reacting a β-arylisoserine derivative of general formula IIa with a haloalkoxycarbonyl ester, in particular 2,2,2-trichloroethoxycarbonyl (TrOC), and then by cyclization in the presence of a strong organic base, such as diazabicycloundecene (DBU). An oxazolidinone derivative of general formula IIIa

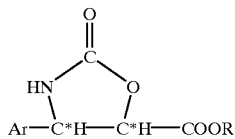

IIIa which Ar and R are defined above, is then obtained.

The derivatives of general formula IIIa can also be obtained by direct synthesis, by reacting the β-arylglycidate derivatives of formula II'a with urea.

The acylated derivatives of general formula II'a are obtained by introducing the R"$_2$—CO— radical according to the usual acylation techniques, in the presence of an appropriate acylating agent, for example an acyl halide of formula R"$_2$—CO—X, in which R"$_2$ is defined above and X represents a halogen, or an anhydride of the corresponding acid.

The dialkyl acetals are obtained according to the usual techniques for the formation of acetals.

3.2 Opening of the oxazoline of general formula IIb

The β-arylisoserine derivative of general formula IIIb

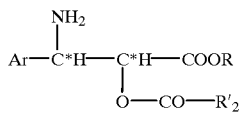

IIIb in which Ar, R and R'$_2$ are defined above, is obtained by hydrolysis of the oxazoline of general formula IIb in acidic medium.

Advantageously, when R'$_2$ represents a lower perhaloalkyl, such as trichloromethyl, the R'$_2$—CO— radical constitutes a protective group for the hydroxyl functional group.

This taxane side chain precursor can then be converted into amides of general formula III'b

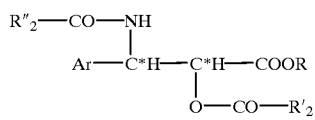

III'b in which

Ar, R, R'$_2$ and R"$_2$ are defined above.

The precursor of the side chain of paclitaxel (R"$_2$=phenyl) or of docetaxel (R"$_2$=t-butoxy) can thus be obtained without distinction.

4. Preparation of the cis-β-arylglycidic acid derivative of formula I

The cis-β-arylglycidic acid derivative of formula I can be prepared according to conventional processes of the state of the art or by simple esterification of cis-β-arylglycidic acid with the corresponding alcohol R—OH. In order to improve the overall yield in the synthesis of taxane chain precursors, a cis-β-arylglycidate derivative of general formula I

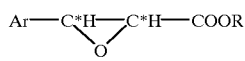

I in which

Ar is defined above and

R represents an optically pure enantiomer of a highly sterically hindered chiral hydrocarbon radical, is prepared in the process according to the invention by reacting the aldehyde of formula

Ar—CHO with the haloacetate of formula

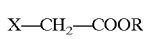

X—CH$_2$—COOR

Ar and R being defined above and

X representing a halogen, in particular a chlorine or a bromine.

Advantageously, the optically pure enantiomer of a highly sterically hindered chiral hydrocarbon radical is a cycloalkyl substituted by one or more alkyl groups, in particular a cyclohexyl.

The method involves a Darzens' reaction through which a mixture of the two diastereoisomers, ester of (2R,3R)-cis-β-arylglycidic acid and (2S,3S)-cis-β-arylglycidic acid and of an optically pure enantiomer of the chiral alcohol R—OH, is obtained, since the Darzens' reaction, carried out with a highly sterically hindered haloacetate, results essentially in the cis form of the β-arylglycidate. Advantageously, the highly sterically hindered chiral hydrocarbon radical will be chosen so that it allows the physical separation of the two diastereoisomers from the reaction mixture, for example by selective crystallization, without requiring a stereospecific separation of the desired enantiomer at the end of the reaction by conventional crystallization or chiral column chromatography methods.

Advantageously, R—OH represents menthol, one of the rare highly sterically hindered chiral alcohols which is economic and commercially available in both its enantiomeric forms.

In the process for the synthesis of a precursor of the taxane side chain, the goal is to prepare a cis-β-phenylglycidate of (2R,3R) configuration. In this case, the highly sterically hindered chiral hydrocarbon radical R will be selected so that the diastereoisomer of the cis-β-phenylglycidate of (2R,3R) configuration crystallizes first from the reaction mixture. When R—OH is menthol, (+)-menthol is advantageously employed.

The asymmetric Darzens' reaction is carried out in the presence of a base, particularly an alkali metal alkoxide, such as potassium tert-butoxide, or an amide, such as lithium bistrimethylsilylamide, in an appropriate solvent, in particular an ether, such as ethyl ether, at a temperature ranging from $-78°$ C. to $25°$ C. The reaction results in a diastereoisomeric mixture composed virtually exclusively of the cis-glycidates, which can reach a yield of greater than 95%, in the region of 97%. Treatment of the isolated product in an appropriate solvent, in particular a methanol/water mixture, makes it possible to readily obtain physical separation of the required diastereoisomers. By fractional crystallization (2 stages), rapid enrichment in the desired diastereoisomer is obtained, with a diastereoisomeric purity of greater than 99%.

The latter point is particularly important because it conditions the isomeric purity of the final taxane, the undesirable diastereoisomers exhibiting their own biological activity which is different from that of the desired taxane.

It is remarkable to observe that the selective use of the two enantiomers of the menthyl ester makes it possible to access, using the same process, the 2 precursor diastereoisomers of the two enantiomers of glycidic acid.

In addition to a fairly high yield of pure isolated diastereoisomer (up to 45%), the diastereoisomeric purity of the major product of the reaction, the ease of implementation of the reaction, the simplicity and the speed of the purification, and the low cost of the reactants and catalysts make the industrial synthesis of this key intermediate in the asymmetric synthesis of β-amino acids easy and economical to access.

When a derivative of general formula I obtained by an asymmetric Darzens' reaction is used in the process according to the invention, the derivatives of general formulae IIa, II'a, IIb, IIIa, IIIb and III'b defined above are then obtained for which R represents an optically pure enantiomer of a highly sterically hindered chiral hydrocarbon radical, such as a cycloalkyl substituted by one or more alkyl groups, in particular a cyclohexyl, preferably menthyl, advantageously (+)-menthyl.

The present invention also relates to these derivatives, which are of use as intermediates in the synthesis of taxane side chains.

It should be noted that the present process constitutes a very rapid access to the substituted chiral oxazolines already described in the literature (WO 94/14787), in 3 stages from commercially available products, instead of 6 to 8 stages.

5. Controlled saponification

A controlled saponification of the derivatives of general formulae IIa, II'a, IIb, IIa, IIIb and III'b is carried out under mild conditions, so as to release the acidic functional group while retaining the structure of the said derivatives, for example in the presence of an alkali metal carbonate in a methanol/water mixture.

After controlled saponification, the derivatives of general formulae IIa, II'a, IIb, IIIa, IIIb and III'b defined above in which R represents a hydrogen atom are obtained, which derivatives can be employed directly in the hemisynthesis of taxanes by coupling with an appropriate baccatin III derivative.

6. Hemisynthesis of taxanes 6.1 Esterification

The present invention thus also relates to a process for the hemisynthesis of taxanes of general formula IV,

in which

C represents a side chain chosen from the radicals of following formulae:

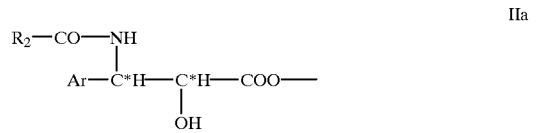

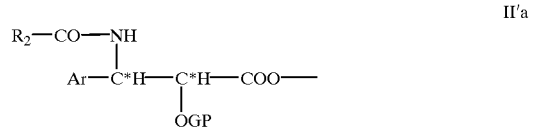

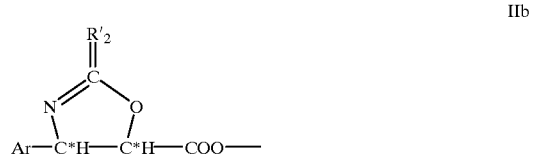

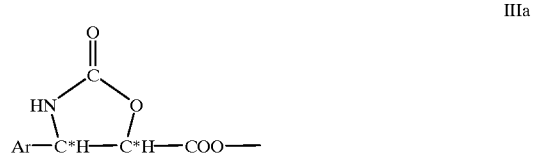

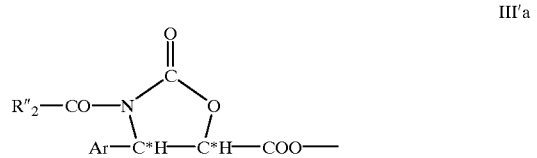

-continued

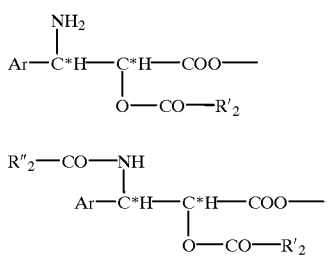
IIIb

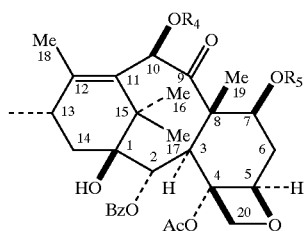
III'b in which Ar, $R_2$, $R'_2$, $R''_2$, $R_3$ and GP are defined above, and B represents a radical derived from baccatin III of general formula V

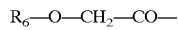 (V)

in which

Ac represents the acetyl radical,

Bz represents the benzoyl radical,

Me represents the methyl radical, $R_4$ represents an acetyl radical or a protective group for the hydroxyl functional group GP1, and $R_5$ represents a protective group for the hydroxyl functional group GP2, by esterification of an appropriate baccatin III derivative of general formula V, carrying a C-13 hydroxyl functional group, with one of the derivatives of general formulae IIa, II'a, IIb, IIIa, III'a, IIIb and III'b defined above, in which R represents a hydrogen atom, under conventional conditions for the preparation of taxanes as defined in the state of the art (in particular: EP-0 253 738, EP-0 336 840, EP-0 336 841, EP-0 495 718, WO 92109589, WO 94/07877, WO 94/07878, WO 94107879, WO 94/10169, WO 94/12482, EP-0 400 971, EP-0 428 376, WO 94/14787).

The GP1 and GP2 protective groups are, independently of one another, conventional groups employed in the hemisynthesis of taxanes, such as trialkylsilyls (EP-0 336 840) or TrOC (EP-0 336 841).

GP1 and GP2 also represent, independently of one another, linear or branched hindered haloalkoxycarbonyl radicals comprising at least one halogen atom. They are advantageously radicals in which the alkyl residue comprises between 1 and 4 carbon atoms and 3 or 4 halogen atoms, preferably chosen from 2,2,2-tribromoethoxycarbonyl, 2,2,2,1-tetrachloroethoxycarbonyl, 2,2,2-trichloro-t-butoxycarbonic and trichloromethoxycarbonyl radicals, radicals which are all more hindered than the haloalkoxycarbonyl (TrOC) used until now to protect taxanes in the 7 position.

GP1 and GP2 also represent, independently of one another, acyl radicals in which the carbon α to the carbonyl functional group carries at least one oxygen atom.

These acyl radicals are described in particular in EP-0 445 021. They are advantageously alkoxy- or aryloxyacetyl radicals of formula

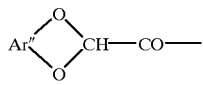

in which $R_6$ represents a sterically hindered alkyl radical, a cycloalkyl radical or an aryl radical, or arylidenedioxyacetyl radicals of formula

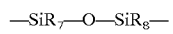

in which Ar" represents an arylidene radical.

Sterically hindered alkyl is preferably understood to mean a linear or branched $C_1$–$C_6$ alkyl radical substituted by one or more bulky substituents chosen from halogens or linear or branched $C_1$–$C_6$ alkyl, linear or branched $C_1$–$C_6$ alkoxy or $C_3$–$C_6$ cycloalkyl or aryl radicals. It will be, for example, a tert-butyl or triphenylmethyl radical.

Cycloalkyl is preferably understood to mean a $C_3$–$C_6$ cycloalkyl radical optionally substituted by one or more bulky substituents chosen from halogens or linear or branched $C_1$–$C_6$ alkyl, linear or branched $C_1$–$C_6$ alkoxy or aryl radicals. Advantageously, it is a cyclohexyl radical substituted by one or more linear or branched $C_1$–$C_6$ alkyl radicals, such as, for example, menthyl, its racemate or its enantiomers and their mixtures in all proportions.

Aryl is preferably understood to mean a phenyl, naphthyl, anthryl or phenantryl radical optionally substituted by one or more bulky substituents chosen from halogens or linear or branched $C_1$–$C_6$ alkyl, linear or branched $C_1$–$C_6$ alkoxy or aryl radicals, in particular the phenyl radical. It is preferably a phenyl radical optionally substituted by one or two above bulky substituents ortho- and ortho'- to the ether bond.

Finally, arylidene is preferably understood to mean a phenylene, naphthylene, anthrylene or phenanthrylene radical optionally substituted by one or more bulky substituents chosen from halogens or linear or branched $C_1$–$C_6$ alkyl, linear or branched $C_1$–$C_6$ alkoxy or aryl radicals, in particular the phenyl radical.

GP1 and GP2 also represent, independently of one another, a trialkylgermanyl radical or together form a divalent radical of formula $$-SiR_7-O-SiR_8-$$

in which $R_7$ and $R_8$, independently of one another, represent a sterically hindered alkyl radical as defined above; in particular, $R_7$ and $R_8$ each represent an isopropyl radical.

6.2 Optional opening

When C represents a radical of formula IIb or IIIa, the oxazoline ring is opened in order to obtain a taxane derivative of formula VI

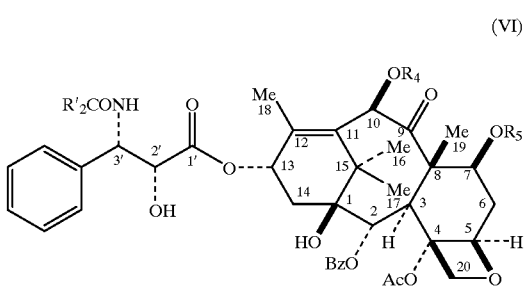

(VI)

in which
Ac, Bz, Me, Ar, R'$_2$, R$_4$ and R$_5$ are defined above.

The IIb, IIIa and III'a radicals are generally opened by hydrolysis in acidic or basic medium. The radical of formula IIb can be opened according to the methods described in the state of the art (in particular WO 94/14787), by hydrolysis in acidic medium, followed by treatment in basic medium, in order to obtain the derivative of general formula VI.

6.3 Deprotection

Finally, the hydroxyls of the derivatives of general formula V or VI are deprotected by replacing the protective groups for the hydroxyl functional group, GP (when C represents the II'a radical), GP1 (when R$_4$ is other than an acetyl) and GP2, by a hydrogen atom according to the usual techniques.

For the derivatives of general formula V in which C represents a radical of formula IIb or IIIa and GP1 and/or GP2 are, independently of one another, conventional groups employed in the hemisynthesis of taxanes, such as trialkylsilyls, the deprotection is carried out simultaneously with the opening described above.

When GP1 and/or GP2 are bulky haloalkoxycarbonyl radicals, deprotection is carried out according to the usual techniques described for TrOC, by the action of zinc or of zinc doped with heavy metals, such as copper, in an organic solvent, in particular in acetic acid, tetrahydrofuran or ethyl alcohol, with or without water.

When GP1 and/or GP2 are acyl radicals in which the carbon a to the carbonyl functional group carries at least one oxygen atom, deprotection is carried out in basic medium by saponification in methanol at low temperature, advantageously with ammonia in methanol at a temperature of less than 10° C., preferably in the region of 0° C.

For the case where C represents a radical of formula IIb, opening of the oxazoline is carried out simultaneously with deprotection in basic medium, in order to result, in one stage, in the corresponding taxane derivative of general formula VI in which R$_4$ represents an acetyl radical or a hydrogen atom and R$_5$ represents a hydrogen atom, in contrast to the opening in acidic medium described in the state of the art, which requires a second stage in basic medium.

The known protective groups are removed using known methods and the oxazoline chain, when it was present, opened out by hydrolysis, giving taxanes in every respect identical to the reference taxanes. By way of example, without, however, limiting the scope of the invention, paclitaxel, 10-deacetyltaxol, cephalomanine and docetaxel can be obtained from the corresponding protected derivatives.

The deblocking of the acyls in which the carbon a to the carbonyl functional group carries at least one oxygen atom was first attempted under the conventional conditions regarded as the mildest, that is to say zinc acetate in methanolic medium at reflux. In this case, as the reaction was complete in a few hours (compared to a few days for acetates), the C-7 epimer resulting from the conventional retroaldolization equilibrium was always isolated, in addition to the desired product. It being presumed that, even under the neutral, indeed slightly acidic, conditions, the main agents responsible were methanol and especially the temperature, we returned to the standard conditions for deblocking acyls described by early writers, by saponification in basic medium in ethanol at low temperature. Under these conditions, no significant epimerization was observed. By way of example, we obtained paclitaxel, 10-deacetyltaxol, cephalomanine and docetaxel, in every respect identical to the reference taxanes, from the corresponding alkoxy- or aryloxyacetylated derivatives.

Finally, it should be noted that all the methods described above, which are nevertheless targeted at improving the overall yield of the hemisynthesis, consist in synthesizing the phenylisoserine chain beforehand, for the purpose of converting it into one of the cyclic structures mentioned above (β-lactams, oxazolidines or oxazolines). Thus, paradoxically, the apparent better performances in the coupling of these cyclic structures only compensates for the fall in overall yield caused by the addition of ring creation stages to the synthetic sequence for the linear chain (i.e., a total of 9 stages). For the general process for the synthesis of taxanes according to the invention, a product such as paclitaxel is obtained in only 5 stages:

(1S,2R,5S)-(+)-menthyl (2R,3R)-3-phenylglycidate
(1S,2R,5S)-(+)-menthyl (4S,5R)-2,4-diphenyl-4,5-dihydroxazole-5-carboxylate
saponification
hemisynthesis (esterification)
opening and deprotection.

Finally, the present invention relates to the synthetic intermediates of general formulae IV, V and VI described above which are of use in the general synthesis of taxanes, a subject of the present invention.

Generally, hydroxycarbon radical is preferably understood to mean, according to the invention, a saturated or unsaturated hydrocarbon radical which can comprise one or more unsaturations, such as an optionally unsaturated linear or branched alkyl, an optionally unsaturated cycloalkyl, an aralkyl or an aryl, it being possible for each optionally to be substituted by one or more substituents, in particular alkyl substituents.

Linear or branched alkyl is preferably understood to mean, according to the invention, a $C_1$–$C_6$ alkyl, in particular chosen from the methyl radical, ethyl radical, propyl radical, isopropyl radical, butyl radical and its various branched isomers, such as, for example, tert-butyl, pentyl radical and hexyl radical and their various branched isomers. This definition also applies to the alkyl residues of the alkoxy or aralkoxy radicals.

Cycloalkyl is preferably understood to mean, according to the invention, a $C_3$–$C_6$ cycloalkyl, in particular chosen from the cyclopropyl, cyclobutyl, cyclopentyl or cyclohexyl radicals.

Aryl is preferably understood to mean, according to the invention, an aromatic or heteroaromatic radical, in particular chosen from the phenyl, naphthyl, anthryl, phenantryl, pyridyl or pyrimidyl radicals and the like.

Finally, halogen is preferably understood to mean chlorine, bromine or iodine. The haloalkoxycarbonyl radicals are preferably radicals in which the alkyl residue comprises between 1 and 4 carbon atoms and 3 or 4 halogen atoms.

The general process for the synthesis of taxanes according to the invention is repeated in Scheme 1 below, wherein R represents (+)-menthyl and $R_2$ or $R'_2$ represent phenyl.

The final stage in the hemisynthesis of taxanes by the process according to the invention is summarized in Schemes 2 and 3 below. Scheme 2 summarizes the synthesis of paclitaxel from derivatives of formula IV defined above in which C represents a radical of formulae IIb or III'a. Scheme 3 summarizes the synthesis of 10-deacetyltaxol from a derivative of formula IV in which C represents a radical of formula IIb.

Of course, the same synthetic schemes can be used for the other definitions of the substituents.

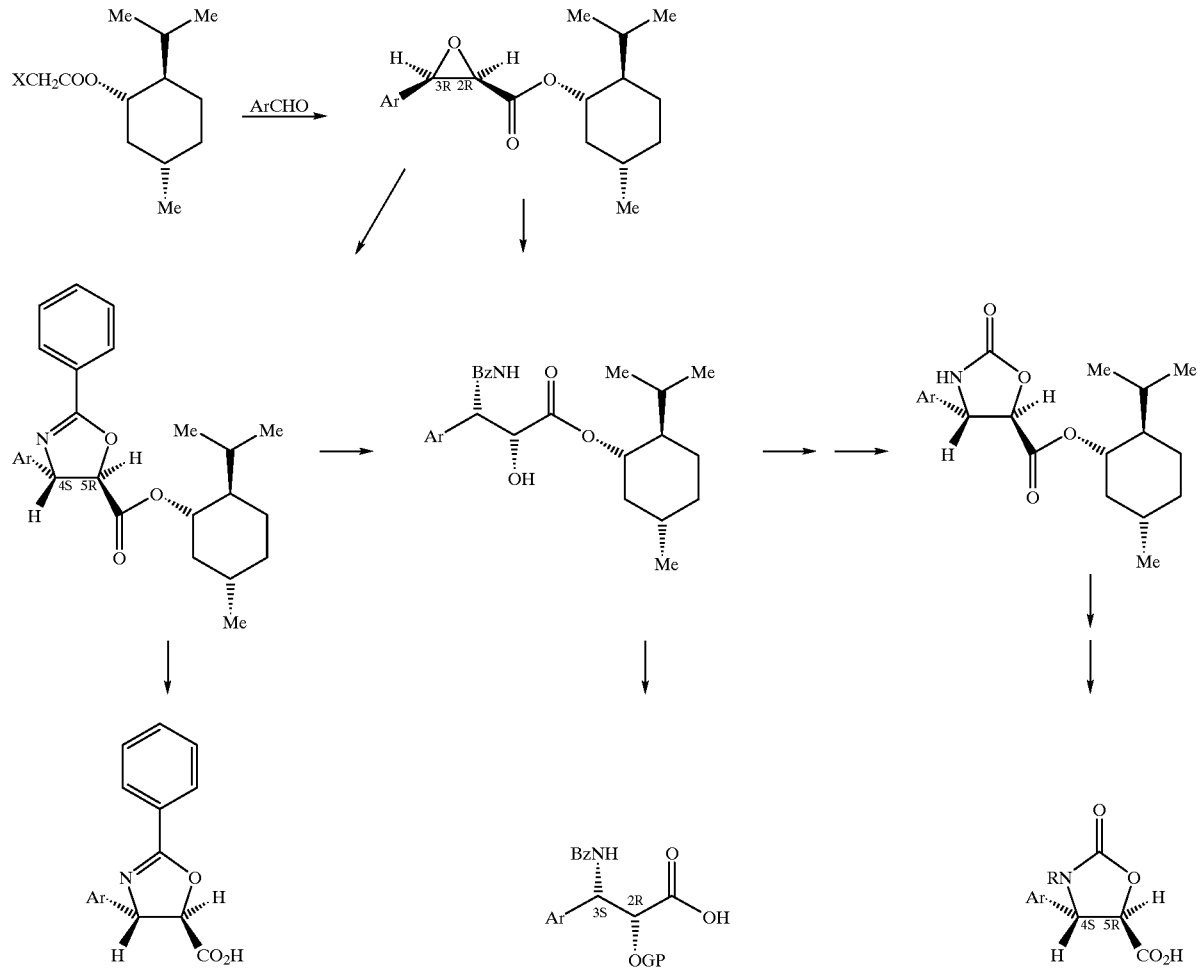

SCHEME 1

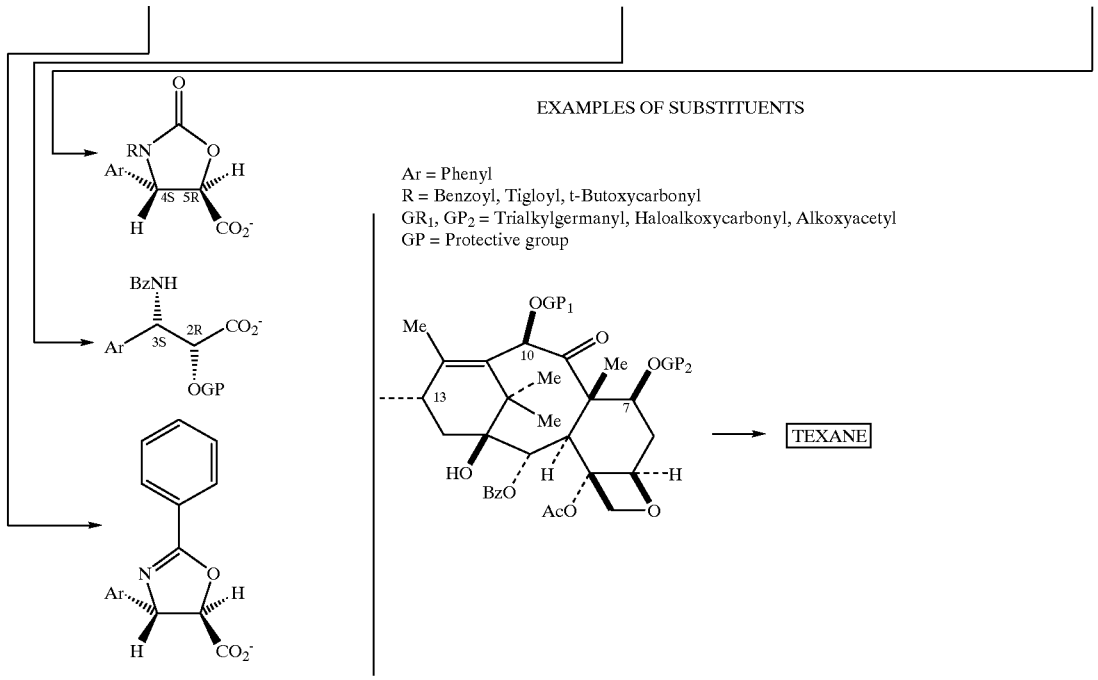
EXAMPLES OF SUBSTITUENTS
Ar = Phenyl
R = Benzoyl, Tigloyl, t-Butoxycarbonyl
GR$_1$, GP$_2$ = Trialkylgermanyl, Haloalkoxycarbonyl, Alkoxyacetyl
GP = Protective group
SCHEME 2
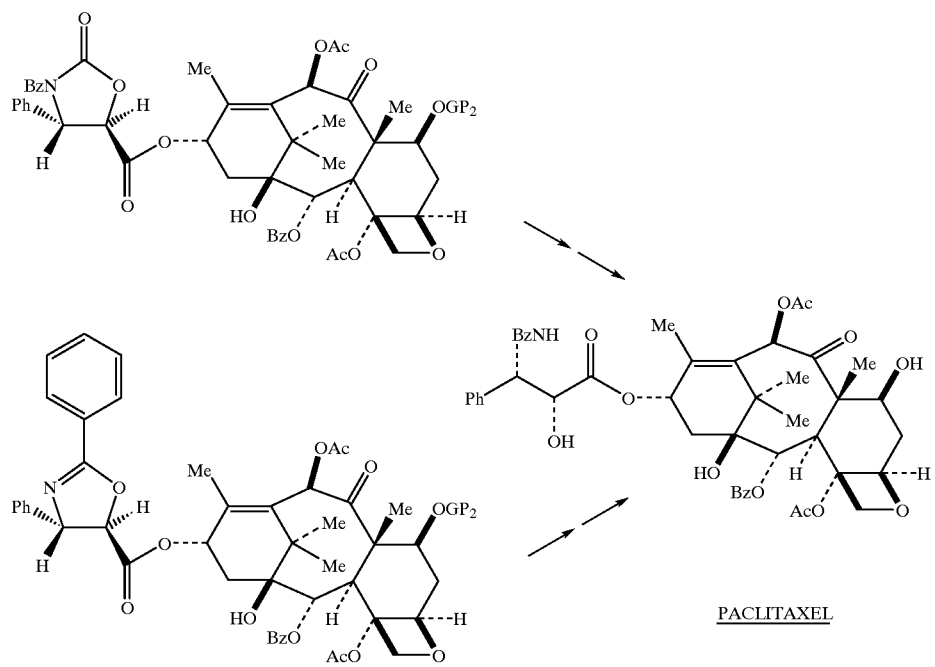
PACLITAXEL

SCHEME 3

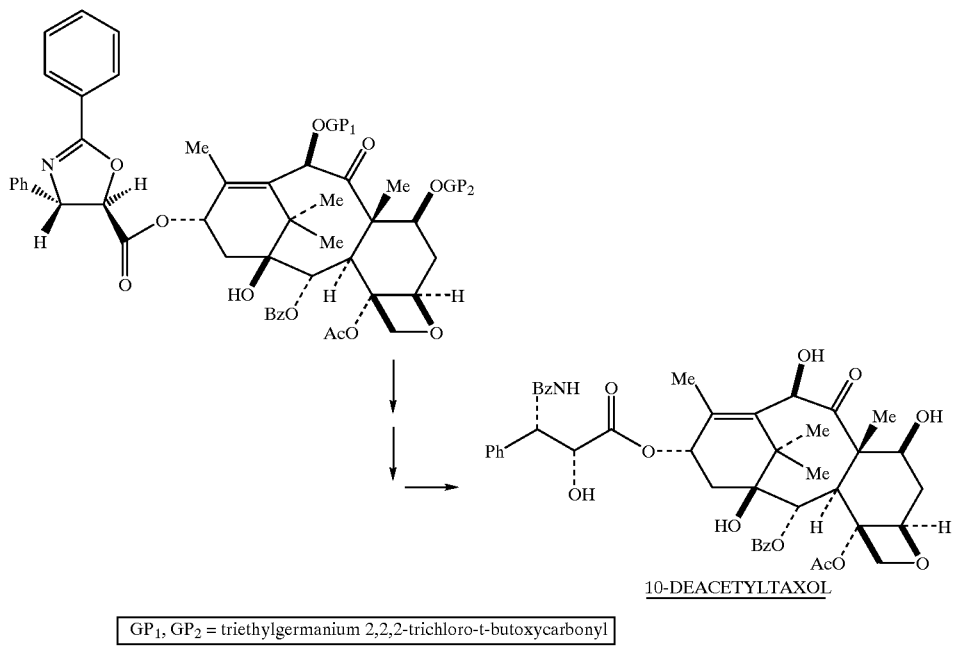

GP₁, GP₂ = triethylgermanium 2,2,2-trichloro-t-butoxycarbonyl

EXAMPLES

I. Taxane side chain precursors

Example 1

(1S,2R,5S)-(+)-Menthyl chloroacetate

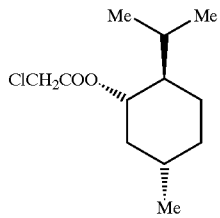

57 mL (0.704 mol) of anhydrous pyridine were added to a stirred solution at room temperature of 100 g (0.640 mol) of (1S,2R,5S)-(+)-menthol in 1 L of dry dichloromethane. After stirring for a few minutes, 56 mL (0.704 mol) of chloroacetyl chloride were subsequently added and the reaction was allowed to continue for 30 min. After monitoring by T.L.C., 50 g of crushed ice were added and the reaction mixture was left vigorously stirring for 1 h. After diluting with 100 mL of dichloromethane, the organic phase was washed several times with a saturated aqueous sodium chloride solution (200 mL), dried over MgSO₄ and then concentrated under reduced pressure. After purifying the crude product thus obtained by silica gel chromatography (15–40 μm) (eluent: cyclohexane/ethyl acetate, 20/1), 146 g of (1S,2R,5S)-(+)-menthyl chloroacetate were obtained in the form of a syrup.

The compound obtained exhibited the following characteristics:

400 MHz $^1$H NMR (CDCl₃) (δ ppm): 4.77 (1H, dt), 4.06 and 4.02 (2H, 2d, J=13.6 Hz), 2.02 (1H, m, J=11.8 Hz), 1.87 (1H, m, J=7 and 2.6 Hz), 1.69 (2H, m), 1.50 (1H, m), 1.43 (1H, m, J=11.7 and 3 Hz), 1.07 (1H, m), 1.02 (1H, q, J=11.8 Hz), 0.92 and 0.90 (6H, 2d, J=6.4 Hz), 0.89 (1H, m), 0.77 (3H, d, J=7 Hz).

Example 2

(1S,2R,5S)-(+)-Menthyl (2R,3R)-3-phenylglycidate

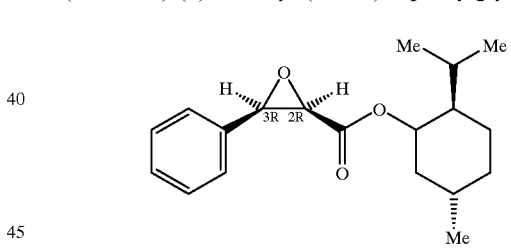

69 mL (0.686 mol) of benzaldehyde were added to a stirred solution at room temperature of 152 g (0.653 mol) of (1S,2R,5S)-(+)-menthyl chloroacetate in 600 mL of anhydrous ethyl ether. After stirring for a few minutes, the solution was cooled to −78° C. under an inert atmosphere, a suspension of 85 g (0.718 mol) of potassium tert-butoxide in 400 mL of anhydrous ethyl ether was subsequently added over 2 h and the reaction mixture was allowed to return to room temperature. After monitoring by T.L.C., the organic part was diluted with 200 mL of dichloromethane, washed several times with a saturated sodium chloride solution, dried over MgSO₄ and concentrated under reduced pressure. 200 g of a crude product were thus obtained in the form of a syrup containing four diastereoisomers (of which two were cis and two were trans), which was subjected as-is to a fractional crystallization.

In a first step, the solution of the crude product in 2 L of methanol was brought to 60° C., to which 700 mL of osmosed water were gradually added, and was left for 16 h at room temperature without being subjected to vibrations.

A yellow-colored lower solid phase rich in trans isomers was discarded and the white crystals of the upper phase, which are rich in cis isomers, were separated by filtration. The crystals thus obtained were redissolved in 2 L of methanol brought to 60° C., 500 mL of osmosed water were added, until a persistent cloudiness was obtained, and the mixture was left for 16 h at room temperature. Three additional crystallizations, carried out according to the same process but with reduced volumes of methanol (1 L) and water (200 mL), were necessary to obtain 23 g of (1S,2R,5S)-(+)-menthyl (2R,3R)-3-phenylglycidate in the crystalline state with an HPLC purity>99% (Yd=12%).

The compound obtained exhibited the following characteristics:

M.p.=104° C.

400 MHz $^1$H NMR (CDCl$_3$) (δ ppm): 7.40 (2H, dd, J=7.8 Hz and 1.7 Hz), 7.32 (3H, m), 4.58 (1H, dt, J=10.9 Hz and 4.2 Hz), 4.26 (1H, d, J=4.6 Hz), 3.83 (1H, d, J=4.8 Hz), 1.6 to 0.85 (9H, m), 0.78 (3H, d, J=7 Hz), 0.75 (3H, d, J=6.4 Hz), 0.62 (3H, d, J 6.9 Hz).

X-ray diffraction of a (1S,2R,5S)-(+)-menthyl (2R,3R)-3-phenylglycidate single crystal for the purpose of the indirect determination of the absolute configuration:

The single crystal was obtained from a crystalline suspension resulting from the addition, while hot, of the non-solvent (water) to a semi-saturated solution of the glycidate in methanol. On slow cooling, fine needles with a purity of 99.95% (HPLC) were deposited by this solution, which needles were stored under moist conditions until the final selection.

The selected sample (fine needle with dimensions 0.12× 0.12×0.40 mm) was studied on a CAD4 Enraf-Nonius automatic diffractometer (molybdenum radiation with graphite monochromator). The unit-cell parameters were obtained by refinement of a set of 25 reflections with a high theta angle. Data collection (2θmax=50°, scanning ω/2θ=1, $t_{max}$=60 s, HKL domain: H 0.6 K 0.14 L 0.28, intensity controls without significant drift (0.1%)) provided 1888 reflections, 1037 of which with I>1.5 σ(I). C$_{19}$H$_{26}$O$_3$: Mr=302.42, orthorhombic, P2$_1$2$_1$2$_1$, a=5.709(11), b=12.908 (4), c=24.433(8) Å, V=1801(5) Å$^{-3}$, Z=4, D$_z$=1.116 Mg.m$^{-3}$, λ(MoKα)=0.70926 Å, $\mu$=0.69 cm$^{-1}$, F(000)=656, T=294 K, final R=0.072 for 1037 observations.

After Lorenz corrections and polarization corrections, the structure was solved using Direct Methods which made it possible to locate the majority of the nonhydrogen atoms of the molecule, the remaining atoms being located by Fourier differences and successive scaling operations. After isotropic refinement (R=0.125) and then anisotropic refinement (R=0.095), most of the hydrogen atoms were located using a Fourier difference (between 0.39 and 0.14 eÅ$^{-3}$), the others being positioned by calculation. The complete structure was refined by whole matrix (x, y, z, β$_{ij}$, for C and O, x, y, z for H; 200 variables and 1037 observations; w=1/σ (F$_o$)$^2$=[σ$^2$(I)+(0.04F$_o^2$)$^2$]$^{-\frac{1}{2}}$) resulting in R=0.080, R$_w$=0.072 and S$_w$=1.521 (residue Δρ≦0.21 eÅ$^{-3}$).

The scattering factors are taken from the International Tables of crystallography [International Tables for X-ray Crystallography (1974), Vol. IV, Birmingham: Kynoch Press (Current distributor D. Reidel, Dordrecht)]. The calculations were carried out on a Hewlett-Packard 9000-710 for the determination of the structure [Sheldrick, G. M. (1985), Crystallographic Computing 3: Data Collection, Structure Determination, Proteins and Databases, edited by G. M. Sheldrick, C. Kruger and R. Goddard, Oxford, Clarendron Press] and on a Digital MicroVax 3100 for the other calculations with the MOLEN suite of programs [Fair, C. K. (1990), MOLEN: An Interactive Intelligent System for Crystal Structure Analysis, Enraf-Nonius, Delft, The Netherlands].

ORTEP DIAGRAM
[Johnson, C.K. (1965), ORTEP, Report ORNL-3794, Oak Ridge National Laboratory, Tennessee, USA]

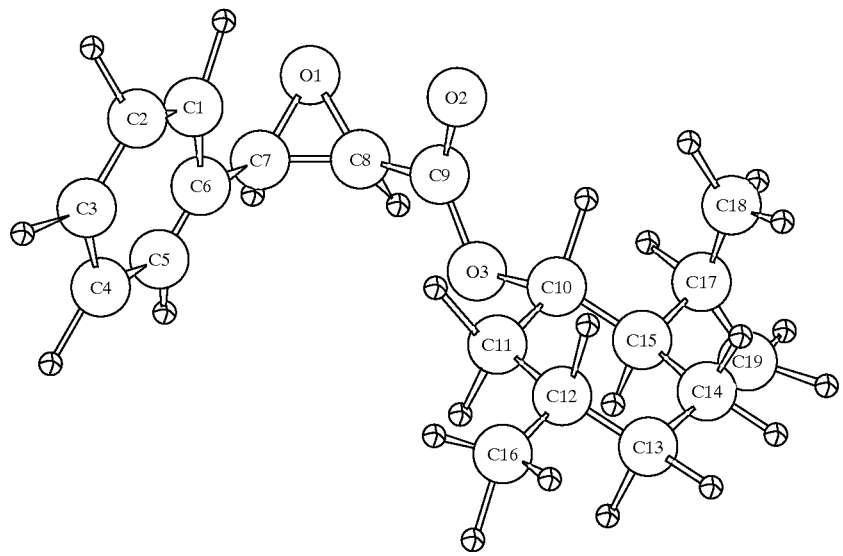

A (1S,2R,5S)-(+)-menthyl (2R,3R)-3-phenylglycidate sample, by treatment with sodium methoxide in methanol, made it possible to obtain the corresponding methyl phenylglycidate, the characteristics of which were as follows:

$[\alpha]_D^{28}$=+12 (c=1.15, chloroform)

400 MHz $^1$H NMR (CDCl$_3$) (δ ppm): 7.40 (2H, d, J=8 Hz), 7.32 (3H, m), 4.26 (1H, d, J=4.6 Hz), 3.84 (1H, d, J=4.6 Hz), 3.55 (3H, s).

Example 3

(1S,2R,5S)-(+)-Menthyl (4S,5R)-2,4-diphenyl-4,5-dihydrooxazole-5-carboxylate

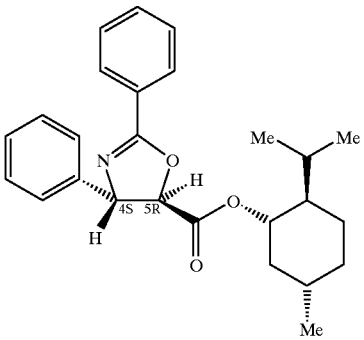

15 mL (0.109 mol) of a 54% solution of tetrafluoroboric acid in ether were added over 10 min to a stirred solution, under an inert atmosphere at −65° C., of 30 g (0.0993 mol) of (1S,2R,5S)-(+)-menthyl (2R,3R)-3-phenylglycidate and 305 mL (2.98 mol) of benzonitrile in 1.5 L of anhydrous dichloromethane. The reaction was allowed to continue at −65° C. for 1 h and, after monitoring by T.L.C., 300 mL of a saturated aqueous sodium hydrogencarbonate solution were added and the reaction mixture was allowed to return to room temperature with stirring. After extracting the aqueous phase with dichloromethane (2×200 mL), the combined organic phases were washed with a saturated sodium chloride solution (200 mL) and with water (50 mL) and dried over MgSO$_4$. After concentrating under reduced pressure and removing the residual benzonitrile under high vacuum at 50° C., the crude product obtained was purified by silica gel chromatography (15–40 μm) (eluent: cyclohexane/ethyl acetate, 20/1).

32 g of (1S,2R,5R)-(+)-menthyl (4S,5R)-2,4-diphenyl-4,5-dihydrooxazole-5-carboxylate were thus isolated in the form of a colorless syrup (Yd=80%) which exhibited the following characteristics:

400 MHz $^1$H NMR (CDCl$_3$) (δ ppm): 8.10 (2H, d, J=7.1 Hz), 7.54 (1H, t, J=7.4 Hz), 7.46 (2H, t, J=7.4 Hz), 7.34 (5H, m), 5.40 (1H, d, J=6.4 Hz), 4.88 (1H, d, J=6.4 Hz), 4.85 (1H, dt, J=10.9 and 4.4 Hz), 2.09 (1H, m), 1.84 (1H, m, J=7 and 2.7 Hz), 1.71 (1H, m), 1.69 (1H, m), 0.94 (3H, d, J=6.5 Hz), 0.9 (1H, m), 0.85 (3H, d, J=7 Hz), 0.77 (3H, d, J=7 Hz).

Example 4

(4S,5R)-2,4-Diphenyl-4,5-dihydrooxazole-5-carboxylic acid

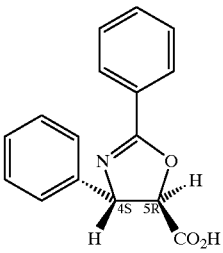

25 mL of a solution of 6 g (43.2 mmol) of potassium carbonate in osmosed water were added to a stirred solution at room temperature of 3.5 g (8.64 mmol) of (1S,2R,5S)-(+)-menthyl (4S,5R)-2,4-diphenyl-4,5-dihydrooxazole-5-carboxylate in methanol (70 mL) and the reaction was left to continue for 16 h at room temperature. After monitoring by T.L.C., the reaction mixture was concentrated under reduced pressure. The aqueous phase thus obtained was washed with dichloromethane (3×100 mL), acidified to pH 2 by slow addition of 20 mL of a 1M aqueous HCl solution and extracted with ethyl acetate (3×100 mL). The combined organic extraction phases were dried (MgSO$_4$) and concentrated under reduced pressure.

2.26 g of (4S,5R)-2,4-diphenyl-4,5-dihydrooxazole-5-carboxylic acid were thus obtained in the form of a white powder (Yd=98%) which exhibited the following characteristics:

$[\alpha]_D^2$=+27.7 (c=0.99, CH$_2$Cl$_2$/MeOH, 1/1)

F=201–202° C.

400 MHz $^1$H NMR (d$_6$-DMSO) (δ ppm): 7.99 (2H, d, J=7.3 Hz), 7.64 (1H, t, J=7.4 Hz), 7.55 (2H, t, J=7.7 Hz), 7.36 (5H, m), 5.40 (1H, d, J=6.3 Hz), 4.99 (1H, d, J=6.4 Hz).

Example 5

(1S,2R,5S)-(+)-Menthyl (2R,3S)-N-benzoyl-3-phenylisoserinate

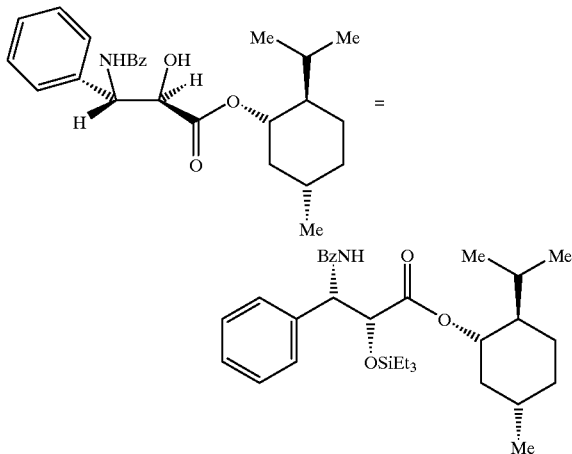

15 mL of a 1 M aqueous HCl solution were added to a stirred solution at room temperature of 1 g (2.47 mmol) of (1S,2R,5S)-(+)-menthyl (4S,5R)-2,4-diphenyl-4,5-dihydrooxazole-5-carboxylate in a mixture of methanol (15 mL) and tetrahydrofuran (15 mL). The reaction mixture was brought for 1 h to reflux and, after monitoring by T.L.C. and returning to room temperature, a saturated aqueous sodium hydrogencarbonate solution (45 mL) was gradually added until a basic pH was obtained. After stirring for 48 h at room temperature, the aqueous phase obtained after concentrating under reduced pressure was extracted with dichloromethane (100 mL). The aqueous phase was washed with a saturated sodium chloride solution (2×50 mL), dried over $MgSO_4$ and concentrated under reduced pressure and the residue obtained was chromatographed on silica gel (15–40 μm) (eluent: dichloromethane/methanol, 95/05).

0.835 g of (1S,2R,5S)-(+)-menthyl (2R,3S)-N-benzoyl-3-phenylisoserinate was thus isolated in the form of a white solid (Yd=80%) which exhibited the following characteristics:

400 MHz $^1$H NMR ($CDCl_3$) (δ ppm): 7.77 (2H, d, J=7.2 Hz), 7.51 (1H, t, J=7.3 Hz), 7.45 (4H, m), 7.36 (2H, t, J=7.2 Hz), 7.29 (1H, t, J=7.2 Hz), 7.04 (1H, d, J=9.2 Hz), 5.78 (1H, dd, J=9.2 and 2.1 Hz), 4.79 (1H, dt, J=10.9 and 4.4 Hz), 4.63 (1H, broad s), 3.35 (1H, broad s), 1.81 (2H, m), 1.67 (3H, m), 1.5 to 1.36 (2H, m), 1.09 to 0.91 (2H, m), 0.89 (3H, d, J=6.9 Hz), 0.77 (3H, d, J=6.5 Hz), 0.74 (3H, d, J=6.9 Hz).

Example 6

(1S,2R,5S)-(+)-Menthyl (2R,3S)-N-benzoyl-O-triethylsilyl-3-phenylisoserinate

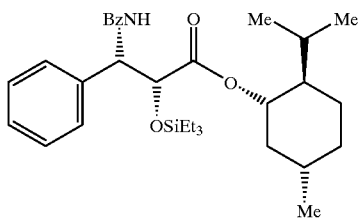

0.255 g (2.08 mmol) of 4-dimethylaminopyridine was added to a solution of 0.8 g (1.89 mmol) of (1S,2R,5S)-(+)-menthyl (2R,3S)-N-benzoyl-3-phenylisoserinate in 10 mL of anhydrous dichloromethane. After stirring for a few minutes at room temperature, 477 μL (2.84 mmol) of triethylsilyl chloride were added over 5 min. After stirring for 1 h at room temperature and monitoring by T.L.C., the reaction mixture was diluted with 100 mL of dichloromethane. The organic phase was washed with a saturated aqueous sodium hydrogencarbonate solution (2×20 mL) and with a saturated sodium chloride solution (50 mL), dried over $MgSO_4$ and concentrated under reduced pressure. After purifying the residue obtained by silica gel chromatography (15–40 μm) (eluent: cyclohexane/ethyl acetate, 10/1), 0.74 g of (1S,2R,5S)-(+)-menthyl (2R,3S)-N-benzoyl-O-triethylsilyl-3-phenylisoserinate was obtained in the form of a colorless syrup (Yd 75%).

The compound obtained exhibited the following characteristics:

400 MHz $^1$H NMR ($CDCl_3$) (δ ppm): 7.82 (2H, d, J=7 Hz), 7.52 (1H, t, J=7.4 Hz), 7.45 (2H, t, J=7 Hz), 7.37 (2H, d, J=7.2 Hz), 7.32 (2H, t, J=7.2 Hz), 7.26 (2H, m), 5.60 (1H, dd), 4.73 (1H, dt, J=11 and 4.3 Hz), 1.88 to 1.67 (m), 1.44 (2H, m), 1.06 and 0.87 (m), 0.80 (m), 0.67 (3H, d, J=7 Hz), 0.62 to 0.34 (m).

Example 7

(2R,3S)-N-Benzoyl-O-triethylsilyl-3-phenylisoserine

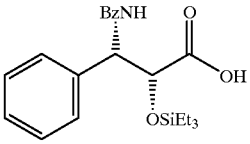

A solution of 0.644 g (4.655 mmol) of sodium carbonate in 10 mL of osmosed water was added to a stirred solution at room temperature of 0.5 g (0.931 mmol) of (1S,2R,5S)-(+)-menthyl (2R,3S)-N-benzoyl-O-triethylsilyl-3-phenylisoserinate in 15 mL of methanol. After stirring for 16 h at room temperature and monitoring by T.L.C., the reaction mixture was concentrated under reduced pressure and the residual aqueous phase was washed with dichloromethane (3×50 mL) and then acidified to pH 2 by slow addition of a 1 M aqueous HCl solution (10 mL). The aqueous phase was extracted with ethyl acetate (3×50 mL) and the combined organic phases were dried over $MgSO_4$ and concentrated under reduced pressure.

0.320 g of (2R,3S)-N-benzoyl-O-triethylsilyl-3-phenylisoserine was obtained in the form of a white powder (Yd=90%) which exhibited the following characteristics:

400 MHz $^1$H NMR ($d_6$-DMSO) (δ ppm): 8.46 (1H, d, J=9.3 Hz), 7.82 (2H, d, J=7.1 Hz), 7.54 (1H, t, J=7.2 Hz), 7.47 (4H, m), 7.32 (2H, t), 7.36 (1H, t), 5.44 (1H, dd, J=9.2 and 5.5 Hz), 4.64 (1H, d, J=5.6 Hz), 0.77 (9H, m), 0.45 (6H, m).

Example 8

(1S,2R,5S)-(+)-Menthyl (2R,3S)-N-benzoyl-O-(2,2,2-trichloroethoxy)carbonyl-3-phenylisoserinate

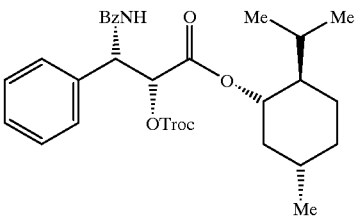

480 mg (3.96 mmol) of 4-dimethylaminopyridine were added to a stirred solution at room temperature under an inert atmosphere of 1.38 g (3.3 mmol) of (1S,2R,5S)-(+)-menthyl (2R,3S)-N-benzoyl-3-phenylisoserinate in 30 mL of anhydrous dichloromethane. After stirring for 10 min, 540 pL (3.96 mmol) of 2,2,2-trichloroethoxycarbonyl chloride were added over 5 min. After stirring for 2 h at room temperature and monitoring by T.L.C., the organic phase was washed with a saturated sodium hydrogencarbonate solution (2×10 mL) and with a saturated sodium chloride solution (10 mL), dried over $MgSO_4$ and concentrated under reduced pressure. After purifying the residue obtained by silica gel chromatography (15–40 μm) (eluent: cyclohexane/ethyl acetate, 5/1), 1.60 g of (1S,2R,5S)-(+)-menthyl (2R,3S)-N-benzoyl-O-(2,2,2-trichloroethoxy)carbonyl-3-phenylisoserinate were obtained in the form of a colorless syrup (Yd=82%).

The compound obtained exhibited the following characteristics:

400 MHz $^1$H NMR (CDCl$_3$) ($\delta$ ppm): 7.82 (2H, d, J=7.4 Hz), 7.53 (1H, t, J=7.4 Hz), 7.44 (4H, m), 7.35 (2H, t, J=7 Hz), 7.29 (1H, t, J=7 Hz), 7.09 (1H, d, J=9.3 Hz), 6.0 (1H, dd, J=9.3 and 2.5 Hz), 5.45 (1H, d, J=2.6 Hz), 4.78 and 4.72 (2H, 2d, J=11.9 Hz), 4.77 (1H, m), 1.85 (1H, m), 1.79 (1H, m), 1.65 (2H, m), 1.43 (1H, m), 1.02 (1H, m), 0.96 (1H, m), 0.86 (1H, m), 0.83 (3H, d, J=7 Hz), 0.78 (3H, d, J=6.5 Hz), 0.68 (3H, d, J=6.9 Hz).

Example 9

(1S,2R,5S)-(+)-Menthyl (4S,5R)-4-phenyloxazolidin-2-one-5-carboxylate

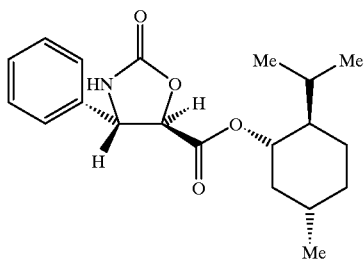

1 mL (7.28 mmol) of 1,8-diazabicylo[5,4,0]undec-7-ene was added to a stirred solution at room temperature under an inert atmosphere of 3.96 g (6.62 mmol) of (1S,2R,5S)-(+)-menthyl (2R,3S)-N-benzoyl-O-(2,2,2-trichloroethoxy) carbonyl-3-phenylisoserinate in 30 mL of anhydrous dichloromethane. After stirring for 30 min at room temperature, the organic phase was washed with 10 mL of a saturated sodium chloride solution, dried over MgSO$_4$ and concentrated under reduced pressure. After purifying the residue by silica gel chromatography (15–40 µm) (eluent: cyclohexane/ethyl acetate, 7/3), 2.18 g of the compound cited in the title were obtained in the form of a yellow syrup (Yd=95%).

The compound obtained exhibited the following characteristics:

400 MHz $^1$H NMR (CDCl$_3$) ($\delta$ ppm): 7.40 (5H, m), 6.09 (1H, s), 4.93 (1H, d, J=5.3 Hz), 4.86 (1H, dt, J=11 and 4.4 Hz), 4.73 (1H, d, J=5.4 Hz), 2.05 (1H, m), 1.81 (1H, m), 1.71 (2H, m), 1.54 to 1.41 (3H, m), 1.07 (2H, m), 0.94 (3H, d, J=6.5 Hz), 0.88 (3H, d, J=7 Hz), 0.77 (3H, d, J=7 Hz).

Example 10

(1S,2R,5S)-(+)-Menthyl (4S,5R)-N-t-butoxycarbonic-4-phenyloxazolidin-2-one-5-carboxylate

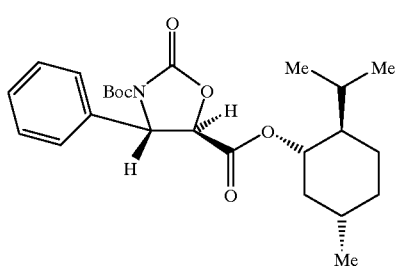

3.8 mL (6.07 mmol) of a 1.6M solution of n-butyllithium in hexane were added to a stirred solution at −40° C. under an inert atmosphere of 1.91 g (5.52 mmol) of (1S,2R,5S)-(+)-menthyl (4S,5R)-4-phenyloxazolidin-3-one-5-carboxylate in 20 mL of anhydrous tetrahydrofuran. After stirring for 10 min at −40° C., a solution of 1.81 g (8.28 mmol) of t-butoxycarbonic anhydride in solution in 5 mL of tetrahydrofuran was added and the reaction mixture was allowed to return to room temperature over 15 min. After diluting with 50 mL of dichloromethane and washing with a 2% aqueous HCl solution until a pH=5 is obtained, the organic phase was dried (MgSO$_4$) and concentrated under reduced pressure. After purifying the crude product by silica gel chromatography (15–40 µm) (eluent: cyclohexane/ethyl acetate, 5/1), 2.12 g of the compound cited in the title were obtained in the form of a colorless syrup (Yd=86%).

The compound thus obtained exhibited the following characteristics:

400 MHz $^1$H NMR (CDCl$_3$) ($\delta$ ppm): 7.45 to 7.26 (5H, m), 5.19 (1H, d, J=3.7 Hz), 4.86 (1H, dt, J=10.9 and 4.5 Hz), 4.66 (1H, d, J=3.7 Hz), 2.05 (1H, m), 1.79 (1H, m), 1.73 (2H, m), 1.62 to 1.24 (3H, m), 1.33 (9H, s), 1.11 (2H, m), 0.94 (3H, d, J=6.5 Hz) and (1H, m), 0.89 (3H, d, J=7 Hz), 0.77 (3H, d, J=7 Hz).

Example 11

(1S,2R,5S)-(+)-Menthyl (4S,5R)-3-N-benzoyl-4-phenyloxazolidin-3-one-5-carboxylate

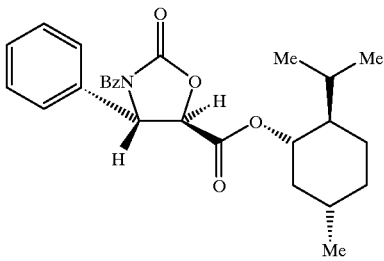

0.25 mL (2.17 mmol) of benzoyl chloride was added to a stirred solution at room temperature under an inert atmosphere of 500 mg (1.45 mmol) of (1S,2R,5S)-(+)-menthyl (4S,5R)-4-phenyloxazolidin-3-one-5-carboxylate and 176 mg (1.16 mmol) of 4-pyrrolidinopyridine in 7 mL of anhydrous dichloromethane. After stirring for 3 h at 50° C., the reaction mixture was brought back to room temperature and diluted with 20 mL of dichloromethane. The organic phase was washed with 10 mL of a saturated sodium chloride solution, dried over MgSO$_4$ and concentrated under reduced pressure. After purifying the crude product by silica gel chromatography (15–40 µm) (eluent: cyclohexane/ethyl acetate, 5/1), 300 mg of the compound cited in the title were obtained in the form of a colorless syrup (Yd=46%).

The compound thus obtained exhibited the following characteristics:

400 MHz $^1$H NMR (CDCl$_3$) ($\delta$ ppm): 8.16 (2H, d, J=7.1 Hz), 7.68 (1H, t), 7.53 (4H, m), 7.43 (3H, m), 5.57 (1H, d, J=4.4 Hz), 4.90 (1H, dt, J=10.9 and 4.4 Hz), 4.85 (1H, d, J=4.3 Hz), 2.07 (1H, m), 1.80 (1H, m), 1.72 (2H, m), 1.47 (3H, m), 1.09 (2H, m), 0.95 (3H, d, J=6.5 Hz), 0.88 (3H, d, J=7 Hz), 0.78 (3H, d, J=7 Hz).

Example 12

(4S,5R)-3-N-Benzoyl-4-phenyloxazolidin-3-one-5-carboxylic acid

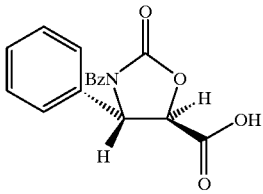

A solution of 75 mg (0.543 mmol) of potassium carbonate in 1 mL of water was added to a stirred mixture at room temperature of 120 mg (0.266 mmol) of (1S,2R,5S)-(+)-menthyl (4S,5R)-3-N-benzoyl-4-phenyloxazolidin-3-one-5-carboxylate in 2 mL of methanol. After stirring for 30 min, the reaction mixture was diluted with 10 mL of water and the aqueous phase was washed with 5 mL of dichloromethane. After acidifying to pH=4 by means of 1 M HCl, the residual aqueous phase was extracted with ethyl acetate (3×10 mL). The combined organic phases were washed with 5 mL of a saturated sodium chloride solution, dried over MgSO$_4$ and concentrated under reduced pressure.

40 mg of (4S,5R)-3-N-benzoyl-4-phenyloxazolidin-3-one-5-carboxylic acid were obtained in the form of a white powder (Yd=52%) which exhibited the following characteristics:

400 MHz $^1$H NMR (d$_6$-DMSO) (δ ppm): 12.98 (1H, broad s), 7.95 (2H, d, J=7.1 Hz), 7.63 (1H, t, J=7.4 Hz), 7.50 (2H, t, J=7.5 Hz), 7.42 (2H, m), 7.37 (3H, m), 4.90 (1H, d, J=5 Hz), 4.77 (1H, d, J=5 Hz).

Example 13

(4S,5R)-4-Phenyloxazolidin-3-one-5-carboxylic acid

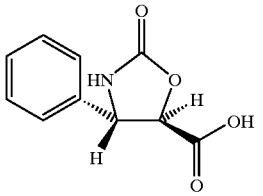

10 mL of a homogeneous solution of 360 mg (8.67 mmol) of NaOH, 3 mL of methanol and 0.5 mL of water in pyridine were rapidly added to a stirred solution at 0° C. under an inert atmosphere of 300 mg (0.867 mmol) of (1S,2R,5S)-(+)-menthyl (4S,5R)-4-phenyloxazolidin-2-one-5-carboxylate, 3 mL of methanol and then 0.5 mL of water in 6.5 mL of pyridine. After stirring for 20 min at 0° C., the reaction mixture was diluted with water (30 mL) and washed with dichoromethane (30 mL). After acidifying to a pH=1, the residual aqueous phase was extracted with ethyl acetate (3×20 mL) and the combined organic phases were dried (MgSO$_4$) and concentrated under reduced pressure.

86 mg of (4S,5R)-4-phenyloxazolidin-3-one-5-carboxylic acid were thus obtained in the form of a yellow syrup (Yd=53%) which exhibited the following characteristics:

400 MHz $^1$H NMR (d$_6$-DMSO) (δ ppm): 13.33 (1H, broad s), 8.46 (1H, s), 7.38 (5H, m), 4.89 (1H, d, J=5 Hz), 4.75 (1H, d, J=5 Hz).

II. Baccatin III derivatives

Example 14

7-O-Triethylsilyl-10-deacetylbaccatin III

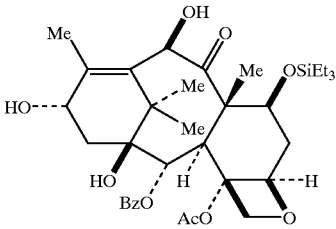

6.2 mL (36.6 mmol) of triethylsilyl chloride were added over 10 min to a stirred solution, at room temperature and under an inert atmosphere, of 10 g (18.3 mmol) of 10-deacetylbaccatin III and 8.17 g (54.9 mmol) of 4-pyrrolidinopyridine in 500 mL of anhydrous dichloromethane. After reacting for 3 h at room temperature, 10 g of crushed ice were added and the mixture was left stirring vigorously for 10 min. The residual organic phase was washed with water (200 mL), dried over MgSO$_4$ and concentrated under reduced pressure.

After treating the crude product obtained with the minimum amount of ethyl acetate, 11.2 g of 7-O-triethylsilyl-10-deacetylbaccatin III were obtained in the crystalline state (Yd=92.3%).

The product thus obtained exhibited the following characteristics:

400 MHz $^1$H NMR (CDCl$_3$) (δ ppm): 8.10 (2H, d, J=7.4 Hz), 7.60 (1H, t, J=7.5 Hz), 7.47 (2H, t, J=7.6 Hz), 5.60 (1H, d, J=7 Hz), 5.17 (1H, d, J=1.9 Hz), 4.96 (1H, d, J=8 Hz), 4.86 (1H, m), 4.41 (1H, dd, J=10.6 and 6.6 Hz), 4.31 and 4.16 (2H, 2d, J=8.4 Hz), 4.26 (1H, d, J=1.9 Hz), 3.95 (1H, d, J=6.9 Hz), 2.48 (1H, ddd, J=14.5, 9.7 and 6.7 Hz), 2.29 (3H, s), 2.27 (2H, m), 2.08 (3H, s), 1.90 (1H, m), 1.73 (3H, s), 1.62 (1H, s), 1.08 (6H, s), 0.94 (9H, t, J=8 Hz), 0.56 (6H, m).

Example 15

7-O-Triethylgermanyl-10-deacetylbaccatin III

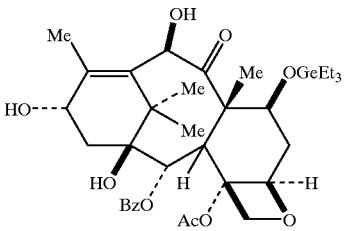

80 μL (0.476 mmol) of triethylgermanyl chloride were added over 10 min to a stirred solution, at room temperature and under an inert atmosphere, of 100 mg (0.183 mmol) of 10-deacetylbaccatin III and 41 mg (0.275 mmol) of 4-pyrrolidinopyridine in 4 ml of anhydrous dichloromethane and the mixture was stirred at 50° C. for 13 h. After cooling the reaction mixture and diluting with 15 mL of dichloromethane, 1 g of crushed ice was added and the mixture was left stirring vigorously for 10 min. The residual organic phase was washed with a saturated sodium hydrogencarbonate solution (5 mL) and a saturated sodium chloride solution (5 mL), dried over MgSO₄ and concentrated under reduced pressure. After chromatographing the crude product on silica gel (15–40 μm) (eluent: cyclohexane/ethyl acetate, 25/75), 67 mg of 7-O-triethylgermanyl-10-deacetylbaccatin III were obtained in the form of a colourless syrup.

The product thus obtained exhibited the following characteristics:

400 MHz ¹H NMR (CDCl₃) (δ ppm): 8.09 (2H, d, J=7.1 Hz), 7.60 (1H, t, J=7.4 Hz), 7.48 (2H, t, J=7.6 Hz), 5.63 (1H, d, J=7.1 Hz), 5.24 (1H, s), 4.99 (1H, d, J=8 Hz), 4.78 (1H, t), 4.32 (1H, d, J=8.3), 4.28 (1H, m), 4.17 (2H, m), 3.97 (1H, d, J=7 Hz), 2.59 (1H, m), 2.30 (3H, s), 2.24 (1H, m), 2.10 (1H, m), 2.03 (3H, s), 1.82 (1H, m), 1.73 (3H, s), 1.11 (9H, m), 1.0 (6H, t, J=7.7 Hz).

Example 16

7-O-(2,2,2-Trichloro-t-butoxycarbonyl)-10-deacetylbaccatin III

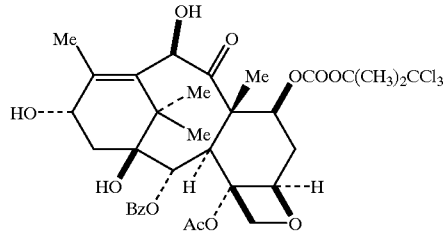

3.3 g (13.8 mmol) of 2,2,2-trichloro-t-butoxycarbonyl chloride were added over 2 h to a stirred solution at 40° C. under an inert atmosphere of 5 g (9.19 mmol) of 10-deacetylbaccatin III and 1.1 mL of anhydrous pyridine in 250 mL of dry dichloromethane. After reacting for an additional 30 min and returning to room temperature, the organic solution was washed with a 2% aqueous HCl solution (30 mL), washed with osmosed water (2×100 mL), dried over MgSO₄ and concentrated under reduced pressure (Yd=55%). After chromatographing the crude product on silica gel (15–40 μm) (eluent: cyclohexane/ethyl acetate, 60/40), 7-O-(2,2,2-trichloro-t-butoxycarbonyl)-10-deacetylbaccatin III was obtained in the form of a white powder.

The product obtained exhibited the following characteristics:

400 MHz ¹H NMR (CDCl₃) (δ ppm): 8.10 (2H, d, J=7 Hz), 7.62 (1H, t, J=7.4 Hz), 7.49 (2H, t, J=7.6 Hz), 5.65 (1H, d, J=6.9 Hz), 5.44 (1H, dd, J=10.8 and 7.3 Hz), 5.39 (1H, d), 4.98 (1H, d, J=7.5 Hz), 4.89 (1H, m), 4.35 and 4.20 (2H, 2d, J=8.4 Hz), 4.10 (1H, d, J=7 Hz), 4.01 (1H, d, J=1.8 Hz), 2.64 (1H, m), 2.31 (3H, s), 2.29 (1H, m), 2.11 (3H, d), 2.05 (2H, m), 1.89 (3H, s), 1.09 (3H, s), 1.07 (3H, s).

Example 17 a) 7-O-Triethylsilylbaccatin III

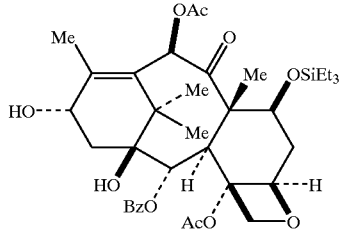

0.54 mL (7.5 mmol) of acetyl chloride was added over 10 min to a stirred solution at room temperature under an inert atmosphere of 1 g (1.5 mmol) of 7-O-triethylsilyl-10-deacetylbaccatin III and 1.25 mL (15 mmol) of pyridine in 15 mL of dry dichloromethane. After reacting for 2 h at room temperature and monitoring by T.L.C., 1 g of crushed ice was added and the mixture was left stirring vigorously for 10 min. The residual organic phase was washed with water (2×10 mL), dried over MgSO₄ and concentrated under reduced pressure. After silica gel chromatography (15–40 μm) (eluent: cyclohexane/ethyl acetate, 60/40), 0.756 g of 7-O-triethylsilylbaccatin III was obtained in the form of a white powder (Yd=70%).

The compound obtained exhibited the following characteristics:

400 MHz ¹H NMR (CDCl₃) (δ ppm): 8.11 (2H, d, J=7.1 Hz), 7.6 (1H, t, J=7.4 Hz), 7.48 (2H, t, J=7.7 Hz), 6.46 (1H, s), 5.63 (1H, d, J=7 Hz), 4.96 (1H, d, J=8.1 Hz), 4.83 (1H, m), 4.49 (1H, dd, J=10.4 and 6.7 Hz), 4.31 and 4.15 (2H, 2d, J=8.3 Hz), 3.88 (1H, d, J=7 Hz), 2.53 (1H, m), 2.29 (3H, s), 2.27 (2H, m), 2.19 (3H, d, J=0.8 Hz), 2.18 (3H, s), 2.12 (1H, d), 1.88 (1H, m), 1.68 (3H, s), 1.65 (1H, s), 1.2 (3H, s), 1.04 (3H, s), 0.92 (9H, t), 0.59 (6H, m).

Example 18

7-O-(2,2,2-Trichloro-t-butoxycarbonyl)baccatin III

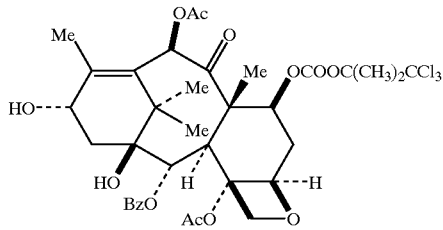

50 μL (0.695 mmol) of acetyl chloride were added to a stirred solution at room temperature under an inert atmosphere of 260 mg of 7-O-(2,2,2-trichloro-t-butoxycarbonyl)-10-deacetylbaccatin III and 127.5 mg (1.04 mmol) of 4-dimethylaminopyridine in 2.5 mL of dry dichloromethane. After reacting for 1 h at room temperature, the organic phase was washed with a 2% aqueous HCl solution until a pH=6 is obtained, dried over MgSO₄ and concentrated under reduced pressure. After chromatographing the residue obtained on silica gel (15–40 μm) (eluent: cyclohexane/ethyl acetate, 6/4), 0.23 g of 7-O-(2,2,2-trichloro-t-butoxycarbonyl)baccatin III was obtained in the solid state (Yd=83%).

The compound obtained exhibited the following characteristics:

400 MHz $^1$H NMR (CDCl$_3$) ($\delta$ ppm): 8.11 (2H, d, J=7.1 Hz), 7.62 (1H, t, J=7.4 Hz), 7.49 (2H, t, J=7.6 Hz), 6.39 (1H, s), 5.64 (1H, d, J=6.9 Hz), 5.61 (1H, dd, J=10.7 and 7.2 Hz), 4.99 (1H, d, J=8.2 Hz), 4.87 (1H, m), 4.33 and 4.16 (2H, 2d, J=8.4 Hz), 4.02 (1H, d, J=6.9 Hz), 2.64 (1H, ddd, J=14.4, 9.5 and 7.2 Hz), 2.30 (3H, s) and (2H, m), 2.17 (3H, s), 2.13 (3H, d, J=0.8 Hz), 2.04 (1H, m), 1.83 (3H, s), 1.63 (1H, s), 1.14 (3H, s), 1.09 (3H, s).

Example 19

7-O-Phenoxyacetyl-10-deacetylbaccatin III

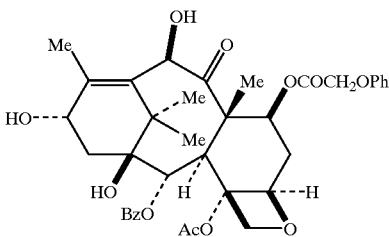

1.05 mL (7.5 mmol) of phenoxyacetyl chloride were added over 10 min to a stirred solution, at room temperature and under an inert atmosphere, of 1.03 g (1.88 mmol) of 10-deacetylbaccatin III and 0.6 mL (7.5 mmol) of anhydrous pyridine in 100 mL of dry dichloromethane. After reacting for 30 min at room temperature and monitoring by T.L.C., the organic solution was washed with a 2% aqueous HCl solution until a pH=2 is obtained, washed with osmosed water (2×50 mL), dried over MgSO$_4$ and concentrated under reduced pressure (Yd=70.5%). After chromatographing the crude product on silica gel (15–40 μm) (eluent: cyclohexane/ethyl acetate, 60/40), 7-O-phenoxyacetyl-10-deacetylbaccatin III was obtained in the form of a white powder.

The product obtained exhibited the following characteristics:

400 MHz $^1$H NMR (CDCl$_3$) ($\delta$ ppm): 8.09 (2H, d, J=7.3 Hz), 7.61 (1H, t, J=7.4 Hz), 7.48 (2H, t, J=7.6 Hz), 7.31 (2H, t, J=7.7 Hz), 6.99 (3H, m), 6.42 (1H, s), 5.61 (1H, d, J=7 Hz), 4.97 (1H, d, J=7.8 Hz), 4.86 (3H, m), 4.44 (1H, dd, J=10.6 and 6.8 Hz), 4.30 and 4.15 (2H, 2d, J=8.4 Hz), 3.86 (1H, d, J=7 Hz), 2.56 (1H, m), 2.27 (3H, s), 2.27 (2H, m), 2.05 ((3H, s), 1.86 (1H, m), 1.68 (3H, s), 1.01 (3H, s), 0.98 (3H, s).

Example 20

7,10-O-Di(phenoxyacetyl)-10-deacetylbaccatin III

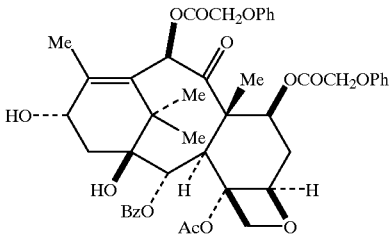

0.5 mL (3.68 mmol) of phenoxyacetyl chloride was added over 10 min to a stirred solution, at room temperature and under an inert atmosphere, of 500 mg (0.92 mmol) of 10-deacetylbaccatin III and 0.6 mL (7.36 mmol) of anhydrous pyridine in 50 mL of dry dichloromethane. After reacting for 6 h at room temperature and monitoring by T.L.C., the solution was washed with a 2% aqueous HCl solution until a pH=2 is obtained, washed with osmosed water (2×20 mL), dried over MgSO$_4$ and concentrated under reduced pressure. After chromatographing the crude product on silica gel (15–40 μm) (eluent: cyclohexane/ethyl acetate, 6/4), 0.55 g of 7-10-O-bis(phenoxyacetyl)-10-deacetylbaccatin III was obtained in the form of a white powder (Yd=74%).

The product obtained exhibited the following characteristics:

400 MHz $^1$H NMR (CDCl$_3$) ($\delta$ ppm): 8.09 (2H, d, J=7.1 Hz), 7.61 (1H, t, J=7.4 Hz), 7.48 (2H, t, J=7.6 Hz), 7.29 (2H, t, J=6.8 Hz), 7.22 (2H, t, J=7.5 Hz), 6.96 (4H, m), 6.84 (2H, d, J=7.9 Hz), 6.42 (1H, s), 5.69 (1H, dd, J=10.5 and 7.1 Hz), 5.60 (1H, d, J=6.9 Hz), 4.96 (1H, d, J=8.2 Hz), 4.84 (1H, t, J=7.4 Hz), 4.8 (2H, s), 4.65 and 4.41 (2H, 2d, J=15.8 Hz), 4.32 and 4.14 (2H, 2d, J=8.4 Hz), 3.98 (1H, d, J=6.8 Hz), 2.65 (1H, m), 2.28 (3H, s), 2.26 (2H, m), 2.09 (3H, s), 1.80 (3H, s) and (1H, m), 0.98 (6H, s).

Example 21

7-O-Phenoxyacetylbaccatin III

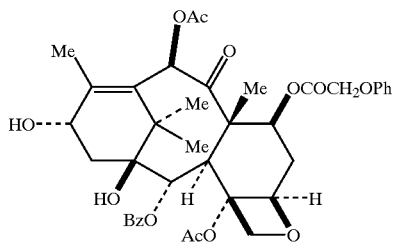

0.233 mL (3.27 mmol) of acetyl chloride was added over 10 min to a stirred solution, at room temperature and under an inert atmosphere, of 1.11 g (1.64 mmol) of 7-O-phenoxyacetyl-10-deacetylbaccatin III in 40 mL of anhydrous pyridine. After reacting for 16 h at room temperature and monitoring by T.L.C., the reaction mixture was diluted with 50 mL of osmosed water and the aqueous phase was extracted with ethyl acetate (3×30 mL). The combined organic phases were washed with water (2×20 mL), dried over MgSO$_4$ and concentrated under reduced pressure (Yd= 84.5%). After silica gel chromatography (15–40 μm) (eluent: cyclohexane/ethyl acetate, 60/40), 7-O-phenoxyacetylbaccatin III was obtained in the crystalline state.

The product obtained exhibited the following characteristics:

400 MHz $^1$H NMR (CDCl$_3$) ($\delta$ ppm): 8.10 (2H, d, J=7.1 Hz), 7.61 (1H, t, J=7.4 Hz), 7.48 (2H, t, J=7.7 Hz), 7.27 (2H, t, J=8 Hz), 6.95 (3H, m), 6.26 (1H, s), 5.71 (1H, dd, J=10.4 and 7.2 Hz), 5.62 (1H, d, J=6.9 Hz), 4.96 (1H, d, J=8.3 Hz), 4.80 (1H, m), 4.81 and 4.53 (2H, 2d, J=16 Hz), 4.32 and 4.14 (2H, 2d, J=8.5 Hz), 4.0 (1H, d, J=6.9 Hz), 2.64 (1H, m), 2.29 (2H, m), 2.28 (3H, s), 2.24 (1H, d, J=5 Hz), 2.16 (3H, s), 2.09 (3H, d, J=0.7 Hz), 1.81 (1H, m), 1.78 (3H, s), 1.13 (3H, s), 1.08 (3H, s).

Example 22

7-10-O-(1,1,3,3-Tetraisopropyl-1,3-disiloxanediyl)-10-deacetylbaccatin III

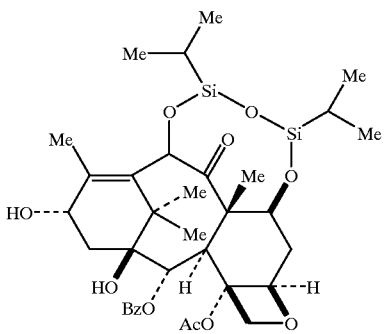

1.28 ml (2.05 mmol) of n-butyllithium as a 1.6M solution in hexane were added over 10 min to a stirred solution, at −40° C. and under an inert atmosphere, of 500 mg (0.93 mmol) of 10-deacetylbaccatin III in 20 mL of anhydrous tetrahydrofuran. After stirring for 5 min, 350 μL (1.12 mmol) of 1,3-dichloro-1,1,3,3-tetraisopropyldisyloxane were added and the reaction mixture was allowed to return to room temperature over 20 min. After stirring for 1 h at room temperature, 225 mg (2.05 mmol) of 4-dimethylaminopyridine were added and the reaction mixture was left stirring for an additional 1 h. After adding 20 mL of a saturated aqueous sodium chloride solution, the mixture was extracted with dichloromethane (3×30 mL). The combined organic phases were washed with a saturated aqueous sodium chloride solution (20 ml), dried over $MgSO_4$ and concentrated under reduced pressure. After purifying by silica gel chromatography (15–40 μm) (eluent: cyclohexane/ethyl acetate, 60/40), 480 mg of 7,10-O-(1,1,3,3-tetraisopropyl-1,3-disyloxanediyl)-10-deacetylbaccatin III were obtained in the amorphous state (Yd=65%).

The product obtained exhibited the following characteristics:

400 MHz $^1$H NMR ($CDCl_3$) (δ ppm): 8.10 (2H, d, J=7.2 Hz), 7.60 (1H, t, J=7.4 Hz), 7.47 (2H, t, J=7.6 Hz), 5.60 (1H, s), 5.59 (1H, d), 4.97 (1H, d, J=7.9 Hz), 4.87 (1H, m), 4.68 (1H, dd, J=10.4 and 6.9 Hz), 4.30 and 4.17 (2H, 2d, J=8.5 Hz), 3.92 (1H, d, J=7.1 Hz), 2.49 (1H, m), 2.28 (3H, s), 2.27 (1H, m), 2.04 (1H, m), 1.91 (1H, m), 1.67 (3H, s), 1.55 (1H, s), 1.32 to 0.85 (34H, m).

Example 23

13-O-[[(4S,5R)-2,4-Diphenyl-4,5-dihydroxazol-5-yl]carbonyl]-7-O-triethylsilylbaccatin III

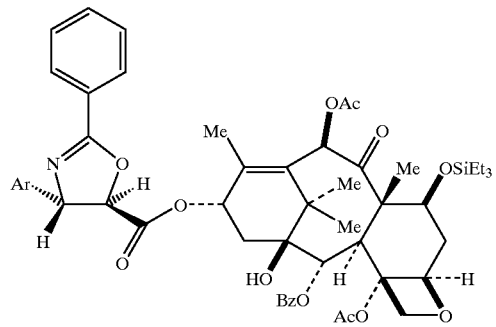

2.06 g (10 mmol) of dicyclohexylcarbodiimide were added to a stirred solution, at room temperature and under an inert atmosphere, of 2.67 g (10 mmol) of (4S,5R)-2,4-diphenyl-4,5-dihydroxazol-5-carboxylic acid in 55 mL of anhydrous toluene. After stirring for 5 min, 3.5 g (5 mmol) of 7-O-triethylsilylbaccatin III and 0.61 g (5 mmol) of 4-dimethylaminopyridine were added and the reaction mixture was brought to 70° C. for 1 h. After returning to room temperature and removing the insoluble materials by filtration, the organic phase was concentrated under reduced pressure. After purifying the crude product by silica gel chromatography (15–25 μm) (eluent: cyclohexane/ethyl acetate, 90/10), 4.62 g of 13-O-[[(4S,5R)-2,4-diphenyl-4,5-dihydroxazol-5-yl]carbonyl-7-O-triethylsilylbaccatin III were obtained in the crystalline state (Yd=97%).

The compound thus obtained exhibited the following characteristics:

400 MHz $^1$H NMR ($CDCl_3$) (δ ppm): 8.23 (2H, d, J=7.2 Hz), 8.07 (2H, d, J=7.3 Hz), 7.63 (1H, t, J=7.4 Hz), 7.58 (1H, t, J=7.4 Hz), 7.49 (4H, m), 7.38 (5H, m), 6.42 ((1H, s), 6.18 (1H, t, J=8.2 Hz), 5.68 (1H, d, J=7.1 Hz), 5.60 (1H, d, J=6.5 Hz), 4.95 (2H, d), 4.50 (1H, dd, J=10.5 and 6.7 Hz), 4.29 (1H, d, J=8.4 Hz), 4.14 (1H, d, J=8.4 Hz), 3.83 (1H, d, J=7.1 Hz), 2.55 (1H, m), 2.37 (1H, dd, J=15.3 and 9.3 Hz), 2.26 (1H, dd, J=15.3 and 8.6 Hz), 2.16 (3H, s),2.07 (3H, s), 1.99 (3H, s), 1.89 (1H, m), 1.72 (1H, s), 1.69 (3H, s), 1.23 (3H, s), 1.19 (3H, s), 0.92 (9H, t, J=8 Hz), 0.57 (6H, m).

Example 24

13-O-[[(4S,5R)-2,4-Diphenyl-4,5-dihydrooxazol-5-yl]carbonyl]-7-O -phenoxyacetylbaccatin III

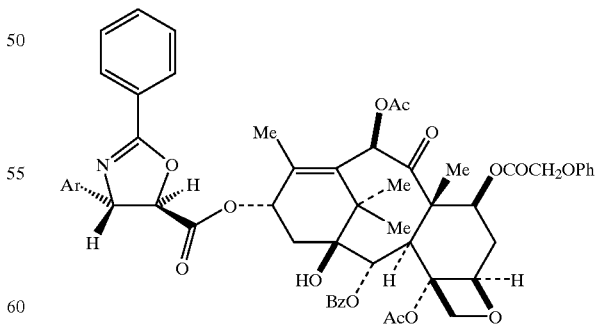

380 mg (1.84 mmol) of dicyclohexylcarbodiimide were added to a stirred solution, at room temperature and under an inert atmosphere, of 490 mg (1.83 mmol) of (4S,5R)-2,4-diphenyl-4,5-dihydrooxazol-5-carboxylic acid in 10 mL of anhydrous toluene. After stirring for 5 min, 660 mg (0.92 mmol) of 7-O-phenoxyacetylbaccatin III and 112 mg (0.92 mmol) of 4-dimethylaminopyridine were added and the reaction mixture was brought to 70° C. for 2 h. After returning to room temperature and removing the insoluble materials by filtration, the organic phase was concentrated under reduced pressure. After purifying the crude product by silica gel chromatography (15–40 μm) (eluent: cyclohexane/ethyl acetate, 99/1), 800 mg of 13-O-[[(4S,5R)-2,4-diphenyl-4,5-dihydrooxazol-5-yl]carbonyl]-7-O-phenoxyacetylbaccatin III were obtained in the crystalline state (Yd=90%).

The compound thus obtained exhibited the following characteristics:

400 MHz $^1$H NMR (CDCl$_3$) (δ ppm): 8.18 (2H, d, J=7 Hz), 8.07 (2H, d, J=7.3 Hz), 7.63 (1H, t, J=7.4 Hz), 7.59–7.32 (1OH, m), 7.28 (2H, t, J=7.5 Hz), 6.94 (3H, m), 6.23 (1H, s) and (1H, m), 5.70 (1H, dd, J=10.4 and 7.1 Hz), 5.67 (1H, d, J=7.3 Hz), 5.58 (1H, d, J=7 Hz), 4.93 (2H, d), 4.79 and 4.53 (2H, 2d, J=15.9 Hz), 4.30 and 4.13 (2H, 2d, J=8.5 Hz), 3.97 (1H, d, J=6.9 Hz), 2.67 (1H, m), 2.38 (1H, dd, J=15.2 and 9.3 Hz), 2.26 (1H, dd, J=15.2 and 8.4 Hz), 2.15 (3H, s), 2.02 (3H, s), 1.95 (3H, s) and (1H, m), 1.80 (3H, s), 1.74 (1H, s), 1.25 (3H, s), 1.17 (3H, s).

Example 25

13-O-[[(4S,5R)-2,4-Diphenyl-4,5-dihydrooxazol-5-yl]carbonyl]-7-O-(2,2,2-trichloro-tbutoxycarbonyl)baccatin III

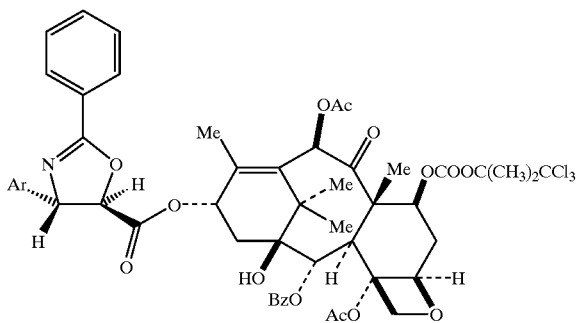

27 mg (0.13 mmol) of dicyclohexylcarbodiimide were added to a stirred solution, at room temperature and under an inert atmosphere, of 35 mg of (4S,5R)-2,4-diphenyl-4,5-dihydrooxazol-5-carboxylic acid in 3 mL of anhydrous toluene. After stirring for 5 min, 51 mg (0.065 mmol) of 7-O-(2,2,2-trichloro-t-butoxycarbonyl)baccatin III and 8 mg (0.065 mmol) of 4-dimethylaminopyridine were added and the mixture was brought to 70° C. for 1 h. After returning to room temperature and removing the insoluble materials by filtration, the organic phase was concentrated under reduced pressure and the residue obtained was purified by silica gel chromatography (15–40 μm) (eluent: cyclohexane/ethyl acetate, 9/1).

0.99 g of the compound cited in the title was thus obtained in the form of a white solid (Yd=67%) which exhibited the following characteristics:

400 MHz$^1$H NMR (CDCl$_3$) (δ ppm): 8.18 (2H, d, J=7.2 Hz), 8.07 (2H, d, J=7.3 Hz), 7.65 (1H, t, J=7.4 Hz), 7.59 (1H, t, J=7.3 Hz), 7.52 (4H, m), 7.39 (5H, m), 6.35 (1H, s), 6.24 (1H, t, J=8.4 Hz), 5.68 (1H, d, J=7.1 Hz), 5.59 (1H, d, J=7 Hz) and (1H, dd), 4.95 (1H, d), 4.94 (1H, d, J=7 Hz), 4.31 and 4.15 (2H, 2d, J=8.4 Hz), 3.97 (1H, d, J=6.9 Hz), 2.64 (1H, m), 2.37 (1H, dd, J=15.1 and 6 Hz), 2.27 (1H, dd, J=15.2 and 8.5 Hz), 2.16 (3H, s), 2.01 (3H, s), 1.98 (3H, s), 1.83 (3H, s), 1.72 (1H, s), 1.25 (3H, s), 1.18 (3H, s).

Example 26

13-O-[[(4S,5R)-2,4-Diphenyl-4,5-dihydrooxazol-5-yl]carbonyl]-7,10-O-(1,1,3,3-tetraisopropyl-1,3-disiloxanediyl)-10-deacetylbaccatin III

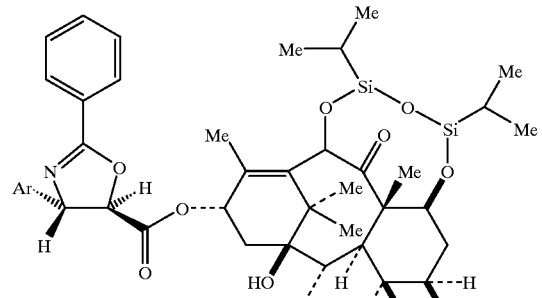

7 mg (0.06 mmol) of dicyclohexylcarbodiimide were added to a stirred solution, at room temperature and under an inert atmosphere, of 4 mg (0.015 mmol) of (4S,5R)-2,4-diphenyl-4,5-dihydrooxazol-5-carboxylic acid in 0.5 mL of anhydrous toluene. After stirring for 5 min, a solution of 5 mg (0.0065 mmol) of 7,10-O-(1,1,3,3-tetraisopropyl-1,3-disiloxanediyl)-10-deacetylbaccatin III and of 1 mg (0.0078 mmol) of 4-dimethylaminopyridine in 1 mL of anhydrous toluene was added. After stirring for 20 min at room temperature, the mixture was brought to 50° C. for an additional 20 min. After returning to room temperature, the organic phase was diluted with 5 mL of dichloromethane, washed with 2 mL of a saturated aqueous sodium chloride solution, dried over MgSO$_4$ and concentrated under reduced pressure. After purifying the crude product by silica gel chromatography (15–25 μm) (eluent: cyclohexane/ethyl acetate, 7/3), 6 mg of the derivative cited in the title were obtained (Yd=90%) in the amorphous state.

The compound obtained exhibited the following characteristics:

400 MHz $^1$H NMR (CDCl$_3$) (δ ppm): 8.21 (2H, d, J=7.2 Hz), 8.07 (2H, d, J=7.6 Hz), 7.63 (1H, t, J=7.5 Hz), 7.59 (1H, t, J=7.4 Hz), 7.50 (2H, t, J=7.4 Hz), 7.39 (5H, m), 6.26 (1H, t), 5.64 (1H, d, J=7 Hz), 5.59 (1H, d, J=6.9 Hz), 5.54 (1H, s), 4.93 (1H, d, J=6.8 Hz) and (1H, m), 4.68 (1H, dd), 4.28 and 4.16 (2H, 2d, J=8 Hz), 3.84 (1H, d, J=7.3 Hz), 2.48 (1H, m), 2.35 and 2.25 (2H, 2dd), 2.02 (3H, s), 1.88 (3H, s) and (1H, m), 1.67 (3H, s), 1.63 (1H, s), 1.30 to 0.90 (34H, m).

Example 27

13-O-[[(4S,5R)-3-N-Benzoyl-4-phenyloxazolidin-3-one-5-yl]carbonyl]-7-O-triethylsilylbaccatin III

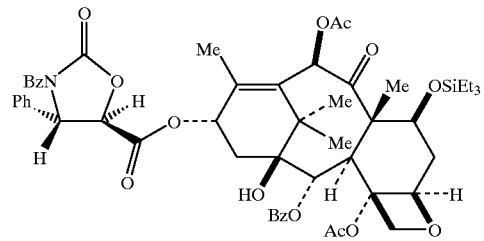

28 mg (0.136 mmol) of dicyclohexylcarbodiimide were added to a stirred solution at room temperature under an inert atmosphere of 40 mg (0.137 mmol) of (4S,5R)-3-N- benzoyl-4-phenyloxazolidin-3-one-5-carboxylic acid in 2 mL of anhydrous toluene. After stirring for 5 min, 30 mg (0.043 mmol) of 7-O-triethylsilylbaccatin III and 8 mg (0.066 mmol) of 4-dimethylaminopyridine were added and the reaction mixture was brought to 60° C. for 13 h. After returning to room temperature, the reaction mixture was diluted with 10 mL of dichloromethane and the organic phase was washed with 5 mL of a saturated sodium chloride solution, dried over $MgSO_4$ and concentrated under reduced pressure. After purifying by silica gel chromatography (15–14 μm) (eluent: cyclohexane/ethyl acetate, 2/1), 13 mg of the derivative cited in the title were obtained in the amorphous state (Yd=31%).

The compound obtained exhibited the following characteristics:

400 MHz $^1$H NMR (CDCl$_3$) (δ ppm): 8.06 (2H, d, J=7.3 Hz), 7.72 (2H, d, J=7 Hz), 7.63 (1H, t, J=7.4 Hz), 7.58 (1H, t, J=7.4 Hz), 7.54 to 7.44 (8H, m), 7.40 (1H, t), 6.44 (1H, s), 6.33 (1H, t), 5.73 (1H, d, J=5.7 Hz), 5.67 (1H, d, J=5.7 Hz), 4.96 (1H, d, J=5.8 Hz), 4.88 (1H, d, J=8.3 Hz), 4.45 (1H, dd, J=10.4 and 6.6 Hz), 4.27 and 4.12 (2H, 2d, J=8.3 Hz), 3.80 (1H, d, J=7 Hz), 2.50 (1H, m), 2.26 (2H, m), 2.19 (3H, s), 2.07 (3H, s), 1.98 (3H, s), 1.85 (1H, m), 1.76 (1H, s), 1.67 (3H, s), 1.24 (3H, s), 1.23 (3H, s), 0.91 (9H, t, J=7.9 Hz), 0.56 (6H, m).

Example 28

13-O-[[(4S,5R)-4-Phenyloxazolidin-3-one-5-yl]carbonyl]-7,1 0-O-di(phenoxyacetyl)-10-deacetylbaccatin III

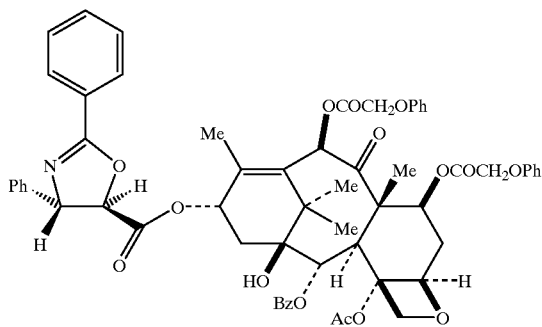

65 mg (0.315 mmol) of dicyclohexylcarbodiimide were added to a stirred solution, at room temperature and under an inert atmosphere, of 78 mg (0.293 mmol) of (4S,5R)-2,4-diphenyl-4,5-dihydrooxazol-5-carboxylic acid in 3 mL of anhydrous toluene. After stirring for 5 min, a solution of 237 mg (0.293 mmol) of 7,10-O-bis(phenoxyacetyl)-10-deacetylbaccatin III and 36 mg (0.295 mmol) of 4-dimethylaminopyridine in 3 mL of toluene was added and the reaction mixture was brought to 60° C. for 1 h. After returning to room temperature and removing the insoluble materials by filtration, the organic phase was concentrated under reduced pressure and the crude product obtained was purified by silica gel chromatography (15–40 μm) (eluent: cyclohexane/ethyl acetate, 1/1).

280 mg of the compound cited in the title were thus obtained in the amorphous state (Yd=90%), which compound exhibited the following characteristics:

400 MHz $^1$H NMR (CDCl$_3$) (δ ppm): 8.18 (2H, d, J=7 Hz), 8.06 (2H, d, J=7.1 Hz), 7.64 (1H, t, J=7.4 Hz), 7.58 (1H, t, J=7.3 Hz), 7.51 (4H, m), 7.39 (5H, m), 7.25 (4H, m), 6.96 (4H, m), 6.85 (2H, d, J=8 Hz), 6.33 (1H, s), 6.19 (1H, t, J=9 Hz), 5.68 (1H, dd, J=10.5 and 7.1 Hz), 5.65 (1H, d, J=6.9 Hz), 5.59 (1H, d, J=7 Hz), 4.93 (2H, d, J=7.1 Hz), 4.79 (2H, s), 4.63 and 4.40 (2H, 2d, J=15.9 Hz), 4.30 and 4.13 (2H, 2d, J=8.4 Hz), 3.94 (1H, d, J=6.9 Hz), 2.68 (1H, m), 2.37 (1H, dd, J=15.3 and 9.3 Hz), 2.24 (1H, dd, J=15.3 and 8.7 Hz), 2.02 (3H, s), 1.95 (3H, s), 1.80 (3H, s) and (1H, m), 1.69 (1H, s), 1.12 (3H, s), 1.01 (3H, s).

III. Hemisynthesis

Example 29

Preparation of paclitaxel a) From 13-O-[[(4S,5R)-2,4-diphenyl-4,5-dihydrooxazol-5-yl]carbonyl]-7-O-triethylsilylbaccatin III 0.6 L (0.6 mol) of a 1 M aqueous HCl solution was added to a stirred solution, at room temperature and under an inert atmosphere, of 90 g (0.095 mol) of 13-O-[[(4S,5R)-2,4-diphenyl-4,5-dihydrooxazol-5-yl]carbonyl]-7-O-triethylsilylbaccatin III in a mixture of tetrahydrofuran (1.2 L) and methanol (1.2 L) and the reaction mixture was stirred at room temperature for 4 h 30. After adding 3.5 L of a saturated aqueous sodium hydrogencarbonate solution, the solution was kept homogeneous by addition of 6 L of tetrahydrofuran and 6 L of water and the reaction mixture was stirred for an additional 1 h 30. After adding 15 L of ethyl acetate and 15 L of osmosed water, the residual aqueous phase was extracted with ethyl acetate (15 L). The organic phase was dried over $MgSO_4$ and concentrated under reduced pressure and the crude product thus obtained was purified by silica gel chromatography (15–40 μm) (eluent: cyclohexane/ethyl acetate, 1/1).

75 g of taxol were thus isolated in the crystalline state (Yd=95%), the characteristics of which were in every respect in accordance with the literature data.

b) From 13-O-[[(4S,5R)-2,4-diphenyl-4,5-dihydrooxazol-5-yl]carbonyl]-7-O-(2,2,2-trichloro-t-butoxycarbonyl) baccatin III 90 μL (0.09 mmol) of a 1 M aqueous HCl solution were added to a stirred solution, at room temperature and under an inert atmosphere, of 15 mg (0.0148 mmol) of 13-O-[[(4S,5R)-2,4-diphenyl-4,5-dihydrooxazol-5-yl]carbonyl]-7-O-(2,2,2-trichloro-t-butoxycarbonyl)baccatin III in a mixture of tetrahydrofuran (0.18 mL) and methanol (0.18 mL) and the reaction mixture was stirred at room temperature for 8 h. After adding 0.6 mL of a saturated aqueous sodium hydrogencarbonate solution, the solution was kept homogeneous by addition of 1 mL of tetrahydrofuran and 1 mL of water and the reaction mixture was stirred for an additional 1 h 30. After adding 2.5 mL of ethyl acetate and 2.5 mL of osmosed water, the residual aqueous phase was extracted with ethyl acetate (2.5 mL). The combined organic phases are dried over $MgSO_4$ and concentrated under reduced pressure.

14 mg of 7-O-(2,2,2-trichloro-t-butoxycarbonyl)taxol are thus obtained in the crude state (Yd=93%), which product was used without additional purification in the following stage.

30 μL (0.525 mmol) of acetic acid and 22.5 mg (0.344 mmol) of zinc powder were added to a stirred solution at room temperature of 13 mg (0.0128 mmol) of 7-O-(2,2,2-trichloro-t-butoxycarbonyl)taxol in 2 mL of ethyl acetate. After stirring for 2 h 30 at room temperature and monitoring by T.L.C., and after diluting the reaction mixture with 3 mL of ethyl acetate, the organic phase was washed with osmosed water (1 mL), with a saturated aqueous sodium hydrogencarbonate solution (1 mL) and again with water, dried over $MgSO_4$ and concentrated under reduced pressure.

After chromatographing the crude product on silica gel (15–40 μm) (eluent: cyclohexane/ethyl acetate, 6/4), 9.5 mg of taxol were thus isolated in the crystalline state (Yd=89%).

What is claimed is:

1. Process for the preparation of taxane side chain precursors in which a cis-β-arylglycidate derivative of general formula I

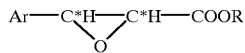

I in which
Ar represents an aryl radical and
R represents a hydrocarbon radical, preferably a linear or branched alkyl or a cycloalkyl optionally substituted by one or more alkyl groups,
is converted, so as to regio- and stereospecifically introduce the β-Nalkylamide and the (-hydroxyl or their cyclic precursors in a single stage by a Ritter reaction, which consists either:
  a of the direct synthesis of a linear chain by reacting a cis-β-arylglycidate derivative of general formula I defined above with a nitrile of formula

in which
  $R_2$ represents an aryl radical, in the presence of a protonic acid and of water, in order to obtain a β-arylisoserine derivative of general formula IIa,

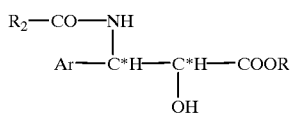

IIa in which Ar, R and $R_2$ are defined above; or
  b of the direct synthesis of a cyclic chain by reacting a cis-β-arylglycidate derivative of general formula I defined above with a nitrile of formula

in which
  $R'_2$ represents $R_2$ defined above or a lower alkyl or lower perhaloalkyl radical, such as trichloromethyl,
  in the presence of a Lewis acid or of a protonic acid, in anhydrous medium, in order to obtain the oxazoline of general formula IIb

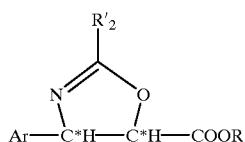

IIb in which Ar, R and $R'_2$ are defined above.

2. Process according to claim 1, characterized in that R represents an optically pure enantiomer of a highly sterically hindered chiral hydrocarbon radical.

3. Process according to claim 2, characterized in that R is one of the enantiomers of the menthyl radical, in particular (+)-menthyl.

4. Process according to one of claims 1 to 3, characterized in that the cis-β-phenylglycidate derivative of general formula I is of (2R,3R) configuration and the derivatives of general formulae IIa and IIb obtained are of (2R,3S) configuration.

5. Process according to claim 4, characterized in that Ar and $R_2$ represent phenyl.

6. Process according to claim 1, characterized in that the protonic acid in stage a is chosen from sulfuric acid, perchloric acid, or tetrafluoroboric acid, the Lewis acid in stage b is chosen from the boron trifluoride acetic acid complex, boron trifluoride etherate, antimony pentachloride, tin tetrachloride, or titanium tetrachloride, and the protonic acid in stage b is tetrafluoroboric acid.

7. Process according to claim 1, characterized in that the β-arylisoserine derivative of general formula IIa is converted by protection of the hydroxyl by an appropriate protective group (GP), in order to obtain a derivative of general formula II'a

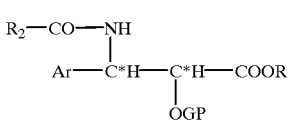

II'a in which Ar, R and $R_2$ are defined in claim 1 and GP represents a protective group for the hydroxyl functional group which is appropriate for the synthesis of taxanes.

8. Process according to claim 1, characterized in that the β-arylisoserine derivative of general formula IIa is converted into a novel oxazolidinone cyclic intermediate of general formula IIIa

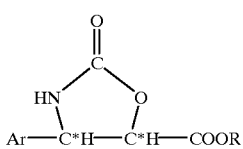

IIIa in which Ar and R are defined in claim 1 by reacting a β-arylisoserine derivative of general formula IIa according to claim 1 with a haloalkoxycarbonyl ester, and then cyclized in the presence of a strong organic base, wherein the strong organic base is optionally diazabicycloundecene (DBU), and optionally converted subsequently into the corresponding amide of general formula III'a

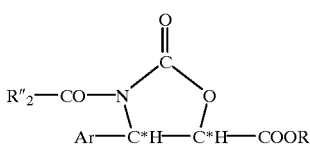

III'a in which Ar and R are defined above and $R''_2$ represents $R'_2$ defined above, an alkoxy radical or a linear or branched alkyl radical comprising at least one unsaturation.

9. Process according to claim 1, characterized in that the oxazoline of general formula IIb is hydrolyzed in acidic medium in order to obtain the β-arylisoserine derivative of general formula IIIb, IIIb

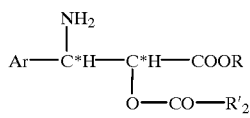

in which Ar, R and R'$_2$ are defined above, and optionally converted subsequently into a corresponding amide of general formula III'b III'b

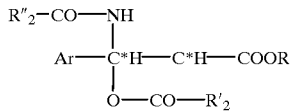

in which Ar, R, R'$_2$ and R"$_2$ are defined above.

10. Process according to claim 1, characterized in that the cis-β-arylglycidate derivative of general formula I

I

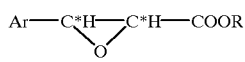

in which

Ar is as defined in claim 1 and

R represents an optically pure enantiomer of a highly sterically hindered chiral hydrocarbon radical, is prepared by reacting the aldehyde of formula

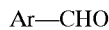

with the haloacetate of formula

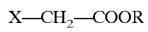

Ar and R being defined above and

X representing a halogen.

11. Process according to any one of claims 1 to 3 and 6 to 10, characterized in that the derivatives of formulae IIa, II'a, IIb, IIIa, III'a, IIIb and III'b, in which R represents a hydrogen atom, are obtained by controlled saponification.

12. Precursor compounds of taxane side chains, characterized in that they are selected from the derivatives of following general formula IIb:

I

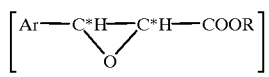

IIa

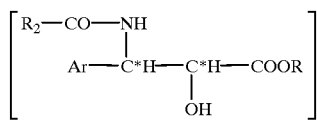

IIb

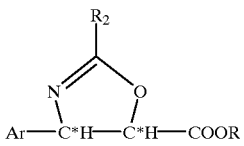

II'a

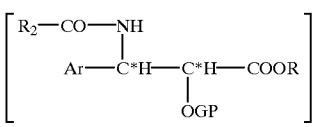

IIIb

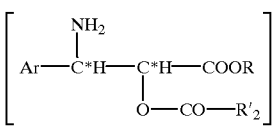

III'b

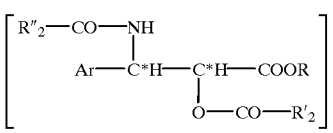

in which Ar and R$_2$
are defined in claim 1, and
R represents an optically pure enantiomer of a highly sterically hindered chiral hydrocarbon radical.

13. Compounds according to claim 12, characterized in that R is one of the enantiomers of the menthyl radical, optionally (+)-menthyl.

14. Compounds according to either one of claim 12 or 13, characterized in that the cis-β-phenylglycidate derivative of general formula I is of (2R,3R) configuration, and the derivative of formula IIb is of (2R, 3S) configuration.

15. Precursor compounds of taxane side chains, characterized in that they are selected from the derivatives of following general formulae IIIa and III'a:

IIIa

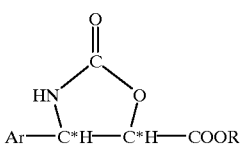

III'a

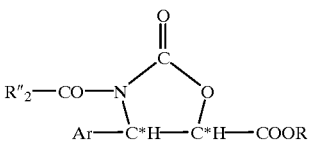

in which

Ar, R and R"$_2$ are defined as in claim 1 or 8, or R represents a hydrogen atom.

16. Compounds according to claim 15, characterized in that they are of (2R,3S) configuration.

17. Process of claim 2, wherein the hydrocarbon radical is a cycloalkyl substituted by one or more alkyl groups.

18. Process of claim 17, wherein the cycloalkyl is a cyclohexyl.

19. Process of claim 7, wherein the protective group is selected from alkoxy ether, aralkoxy ether, aryloxy ether haloalkoxycarbonyl radicals.

20. Process of claim 19, wherein the haloalkoxycarbonyl radicals are selected from methoxymethyl, 1-ethoxyethyl, benzyloxymethyl or (β-trimethyl-silylethoxy) methyl groups, tetrahydropyranyl radicals, β-alkoxycarbonyl radicals, β-halogenated ethers, alkylsilyl ethers, and alkoxyacetyl, aryloxyacetyl, haloacetyl or formyl radicals.

21. Process of claim 10, wherein the halogen is chlorine or bromine.

22. Process according to claim 4, characterized in that the derivatives of formulae IIa, II'a, IIb, IIIa, III'a, IIIb and III'b, in which R represents a hydrogen atom, are obtained by controlled saponification.

23. Process according to claim 5, characterized in that the derivatives of formulae IIa, II'a, IIb, IIIa, III'a, IIIb and III'b, in which R represents a hydrogen atom, are obtained by controlled saponification.

* * * * *

UNITED STATES PATENT AND TRADEMARK OFFICE
CERTIFICATE OF CORRECTION

PATENT NO.    : 6,265,587 B1
DATED         : July 24, 2001
INVENTOR(S)   : Luc Chanteloup et al.

It is certified that error appears in the above-identified patent and that said Letters Patent is hereby corrected as shown below:

Column 39,
Line 18, delete "(" and insert -- α --.
Line 21, "a" (first occurrence) should read -- a --.
Line 39, "b"should read -- b --.

Column 41,
Line 48, after "above" insert a comma -- , --.

Column 42,
Line 56, delete "or 8".

Signed and Sealed this

Seventh Day of January, 2003

JAMES E. ROGAN
*Director of the United States Patent and Trademark Office*